United States Patent
Schaap et al.

(10) Patent No.: US 6,284,899 B1
(45) Date of Patent: Sep. 4, 2001

(54) CHEMILUMINESCENT DIALKYL-SUBSTITUTED 1,2-DIOXETANE COMPOUNDS, METHODS OF SYNTHESIS AND USE

(75) Inventors: Arthur Paul Schaap, Grosse Pointe Park; Hashem Akhavan-Tafti, Sterling Heights, both of MI (US)

(73) Assignees: The Board of Governors of Wayne State University, Detroit; Lumigen, Inc., Southfield, both of MI (US)

( * ) Notice: Subject to any disclaimer, the term of this patent is extended or adjusted under 35 U.S.C. 154(b) by 290 days.

(21) Appl. No.: 08/999,930

(22) Filed: Nov. 28, 1997

Related U.S. Application Data

(60) Continuation of application No. 08/703,973, filed on Aug. 28, 1996, now abandoned, which is a division of application No. 08/344,124, filed on Nov. 23, 1994, now Pat. No. 5,578,253.

(51) Int. Cl.$^7$ ................................................ C07D 305/14
(52) U.S. Cl. ............................................................ 549/332
(58) Field of Search ............................................. 549/332

(56) References Cited

U.S. PATENT DOCUMENTS

| | | | |
|---|---|---|---|
| 4,952,707 | 8/1990 | Edwards | 549/221 |
| 4,959,182 | 9/1990 | Schaap | 252/700 |
| 4,962,192 | 10/1990 | Schaap | 536/18.1 |
| 5,004,565 | 4/1991 | Schaap | 549/510 |
| 5,068,339 | 11/1991 | Schaap | 548/110 |
| 5,112,960 | 5/1992 | Bronstein | 549/221 |
| 5,132,204 | 7/1992 | Urdea | 549/218 |
| 5,145,772 | 9/1992 | Voyta | 436/71 |
| 5,220,005 | 6/1993 | Bronstein | 549/221 |
| 5,248,618 | 9/1993 | Haces | 549/332 |
| 5,326,882 | 7/1994 | Bronstein | 549/16 |
| 5,650,525 | 7/1997 | Matsumoto | 549/510 |

FOREIGN PATENT DOCUMENTS

| | | |
|---|---|---|
| 0671395 | 9/1995 | (EP) . |
| 8800695 | 1/1988 | (WO) . |
| 9410258 | 5/1994 | (WO) . |
| 9421821 | 9/1994 | (WO) . |

OTHER PUBLICATIONS

K.R. Kopecky and C. Mumford, Can. J. Chem., 47, 709 (1969).

P.D. Bartlett and A.P. Schaap, J. Am. Chem. Soc., 92, 3223 (1970).

Mazur and Foote (S. Mazur and C.S. Foote, J. Am. Chem. Soc., 92, 3225 (1970).

K.R. Kopecky in Chemical and Biological Generation of Excited States, W. Adam and G. Cilento, (Eds.), Academic Press, New York, p. 85, 1982.

A.P. Schaap, P.A. Burns and K.A. Zaklika, J. Am. Chem. Soc., 99, 1270 (1977).

A. Baumstark in Advances in Oxygenated Processes, JAI Press, Greenwich, CT, 1988; vol. 1, pp. 31–84.

W. Adam, L.A. Encarnacion and K. Zinner, Chem. Ber., 116, 839 (1983).

G.G. Geller, C.S. Foote and D.B. Pechman, Tetrahedron Lett., 673 (1983).

W. Adam, L.A. Arias and D. Schuetzow, Tetrahedron Lett., 2835 (1982).

J.H. Wieringa, J. Strating, H. Wynberg and W. Adam, Tetrahedron Lett., 169 (1972).

N.J. Turro, G. Schuster, H.C. Steinmetzer, G.R. Faler and A.P. Schaap, J. Amer. Chem. Soc., 97, 7110 (1975).

F. McCapra, I. Beheshti, A. Burgord, R.A. Hann and K.A. Zaklika, J. Chem. Soc., Chem. Comm., 944 (1977).

A.P. Schaap and S. Gagnon, J. Amer. Chem. Soc., 104, 3504 (1982).

T. Wilson, Int. Rev. Sci.: CHem., Ser. Two, 9, 265 (1976).

T. Wilson, M.E. Landis, A.L. Baumstark, and P.D. Bartlett, J. Amer. Chem. Soc., 95, 4765 (1973).

P.D. Bartlett, A.L. Baumstark, and M.E. Landis, J. Amer. Chem. Soc., 96, 5557 (1974).

A.P. Schaap, T.S. Chen, R.S. Handley, R. DeSilva, and B.P. Giri, Tetrahedron Lett., 1155 (1987).

W. Adam, R. Fell, M.H. Schulz, Tetrahedron, 49 (11), 2227–38 (1993).

W. Adam, M.H. Schulz, Chem. Ber., 125, 2455–61 (1992).

P.D. Bartlett and M. Ho, J. Am. Chem. Soc., 96 627 (1975).

P. Lechtken, Chem. Ber., 109, 2862 (1976).

A.P. Schaap, R.S. Handley, and B.P. Giri, Tetrahedron Lett., 935 (1987).

A.P. Schaap, M.D. Sandison, and R.S. Handley, Tetrahedron Lett., 1159 (1987).

A.P. Schaap, Photochem. Photobiol., 47S, 50S (1988).

M. Ryan, J.C. Huang, O.H. Griffith, J.F. Keana, J.J. Volwerk, Anal. Biochem., 214(2), 548–56 (1993).

A.P. Schaap, H. Akhavan and L.J. Romano, Clin. Chem., 35(9), 1863 (1989).

M. Matsumoto and H. Suganuma, J. Chem. Soc. Chem. Comm., 2449–50, (1994).

*Primary Examiner*—Amelia Owens
(74) *Attorney, Agent, or Firm*—Richard S. Handley

(57) ABSTRACT

A chemiluminescent assay method and compositions are described which use a dialkyl-substituted dioxetane which is deprotected to trigger a chemiluminescent reaction. Chemiluminescent 1,2-dioxetane compounds substituted on the dioxetane ring with two nonspirofused alkyl groups which can be triggered by a reagent to generate light are disclosed. Dialkyl-substituted dioxetanes are useful for the detection of triggering agents including enzymes. The enzyme may be present alone or linked to a member of a specific binding pair in an immunoassay, DNA probe assay or other assay where the enzyme is bound to a reporter molecule.

32 Claims, 8 Drawing Sheets

— DI-ISOPROPYL ACETOXY DIOX + KOH/DMSO CL

Dioxetane 2f    Dioxetane 2k

US 6,284,899 B1

CHEMILUMINESCENT DIALKYL-SUBSTITUTED 1,2-DIOXETANE COMPOUNDS, METHODS OF SYNTHESIS AND USE

This application is a continuation of Ser. No. 08/703,973 filed Aug. 28, 1996 now abandoned which is a divisional of Ser. No. 08/344,124 filed Nov. 23, 1994 U.S. Pat. No. 5,578,253.

BACKGROUND OF THE INVENTION (1) Field of the Invention

The present invention relates to chemiluminescent 1,2-dioxetane compounds that can be triggered by reagents including enzymes and other chemicals to generate light. In particular, the present invention relates to stable aryl group-substituted 1,2-dioxetanes that contain a triggerable X-oxy group (OX) which is a substituent of the aryl group, in which the stable 1,2-dioxetane forms an unstable dioxetane compound by removal of X, which decomposes to produce light and two carbonyl compounds.

(2) Description of Related Art a. Preparation of 1,2-Dioxetanes. Kopecky and Mumford reported the first synthesis of a dioxetane (3,3,4-tri-methyl-1,2-dioxetane by the base-catalyzed cyclization of a β-bromohydroperoxide, which, in turn, is prepared from the corresponding alkene (K. R. Kopecky and C. Mumford, *Can. J. Chem.*, 47, 709 (1969)). Although this method has been used to produce a variety of alkyl and aryl-substituted 1,2-dioxetanes, it can not be used for the preparation of dioxetanes derived from vinyl ethers, vinyl sulfides and enamines.

An alternate synthetic route to 1,2-dioxetanes, especially those derived from vinyl ethers, vinyl sulfides and enamines was independently reported by Bartlett and Schaap (P. D. Bartlett and A. P. Schaap, *J. Am. Chem. Soc.*, 92, 3223 (1970)) and Mazur and Foote (S. Mazur and C. S. Foote, *J. Am. Chem. Soc.*, 92, 3225 (1970)). Photochemical addition of a molecule of oxygen to the appropriate alkene compound in the presence of a photosensitizer produces 1,2-dioxetanes in high yield. This method has been used to produce a large number of dioxetane compounds (K. R. Kopecky in *Chemical and Biological Generation of Excited States*, W. Adam and G. Cilento, (Eds.), Academic Press, New York, p. 85, 1982).

Two limitations of this method have been reported. Certain alkenes with aromatic substituents were found to produce six membered ring peroxides known as endoperoxides on photooxygenation (A. P. Schaap, P. A. Burns and K. A. Zaklika, *J. Am. Chem. Soc.*, 99, 1270 (1977)). Alkenes with reactive allylic hydrogens frequently undergo an alternate reaction, the "ene" reaction, producing an allylic hydroperoxide instead of a dioxetane (A. Baumstark in Advances In Oxygenated Processes, JAI Press, Greenwich, Conn., 1988; Vol.1, pp 31–84).

b. Thermally Stable Dioxetanes from Sterically Hindered Alkenes. The dioxetane derived from the hindered alkene adamantylideneadamantane which was discovered by Wynberg (J. H. Wieringa, J. Strating, H. Wynberg and W. Adam, *Tetrahedron Lett.*, 169 (1972) was shown to have an activation energy for decomposition of 37 kcal/mol and a half life ($t_{1/2}$) at 25° C. of several years (N. J. Turro, G. Schuster, H. C. Steinmetzer, G. R. Faler and A. P. Schaap, *J. Amer. Chem. Soc.*, 97, 7110 (1975)). Others have shown that a spiro-fused polycyclic group such as the adamantyl group can help to increase the stability of dioxetanes derived from amino-substituted alkenes (F. McCapra, I. Beheshti, A. Burford, R. A. Hann and K. A. Zaklika, *J. Chem. Soc., Chem. Comm.*, 944 (1977)), vinyl ethers (W. Adam, L. A. Encarnacion and K. zinner, *Chem. Ber.*, 116, 839 (1983)) and vinyl sulfides (G. G. Geller, C. S. Foote and D. B. Pechman, *Tetrahedron Lett.*, 673 (1983); W. Adam, L. A. Arias and D. Schuetzow, *Tetrahedron Lett.*, 2835 (1982)) which would be unstable without this group.

c. Chemical Triggering of Dioxetanes. The first example in the literature is described in relation to the hydroxy-substituted dioxetane derived from the 2,3-diaryl-1,4-dioxene (A. P. Schaap and S. Gagnon, *J. Amer. Chem. Soc.*, 104, 3504 (1982)). However, the hydroxy-substituted dioxetane and any other examples of the dioxetanes derived from the diaryl-1,4-dioxenes are relatively unstable having half-lives at 25° C. of only a few hours. Further, these non-stabilized dioxetanes are destroyed by small quantities of amines (T. Wilson, *Int. Rev. Sci.: Chem., Ser. Two*, 9, 265 (1976)) and metal ions (T. Wilson, M. E. Landis, A. L. Baumstark, and P. D. Bartlett, *J. Amer. Chem. Soc.*, 95, 4765 (1973); P. D. Bartlett, A. L. Baumstark, and M. E. Landis, *J. Amer. Chem. Soc.*, 96, 5557 (1974)), both components used in the aqueous buffers for biological assays.

Examples of the chemical triggering of adamantyl-stabilized dioxetanes were first reported in U.S. patent application (A. P. Schaap, patent application Ser. No. 887, 139, filed Jul. 17, 1986) and a paper (A. P. Schaap, T. S. Chen, R. S. Handley, R. DeSilva, and B. P. Giri, *Tetrahedron Lett.*, 1155 (1987)). These dioxetanes exhibit thermal half-lives of years but can be triggered to produce efficient chemiluminescence on demand. Moderately stable benzofuranyl dioxetanes substituted with trialkylsilyl and acetyl-protected phenolic groups which produce weak chemiluminescence have also been reported (W. Adam, R. Fell, M. H. Schulz, *Tetrahedron*, 49(11), 2227–38 (1993); W. Adam, M. H. Schulz, *Chem. Ber.*, 125, 2455–61 (1992)). The stabilizing effect of other rigid polycyclic groups has also been reported (P. D. Bartlett and M. Ho, *J. Am. Chem. Soc.*, 96, 627 (1975); P. Lechtken, *Chem. Ber.*, 109, 2862 (1976)). A PCT application, WO 94/10258 discloses chemical triggering of dioxetanes bearing various rigid polycyclic substituents.

d. Enzymatic Triggering of Adamantyl Dioxetanes. Dioxetanes which can be triggered by an enzyme to undergo chemiluminescent decomposition are disclosed in U.S. patent application (A. P. Schaap, patent application Ser. No. 887,139) and a series of papers (A. P. Schaap, R. S. Handley, and B. P. Giri, *Tetrahedron Lett.*, 935 (1987); A. P. Schaap, M. D. Sandison, and R. S. Handley, *Tetrahedron Lett.*, 1159 (1987) and A. P. Schaap, *Photochem. Photobiol.*, 47S, 50S (1988)). The highly stable adamantyl-substituted dioxetanes bearing a protected aryloxide substituent are triggered to decompose with emission of light by the action of an enzyme in an aqueous buffer to give a strongly electron-donating aryloxide anion which dramatically increases the rate of decomposition of the dioxetane. As a result, chemiluminescence is emitted at intensities several orders of magnitude above that resulting from slow thermal decomposition of the protected form of the dioxetane. U.S. Pat. No. 5,068,339 to Schaap discloses enzymatically triggerable dioxetanes with covalently linked fluorescer groups. Decomposition of these dioxetanes results in enhanced and red-shifted chemiluminescence through intramolecular energy transfer to the fluorescer. U.S. Pat. No. 4,952,707 to Edwards discloses enzymatically triggerable dioxetanes bearing an adamantyl group and 2,5- or 2,7-disubstituted naphthyl groups. U.S. Pat. Nos. 5,112,960, 5,220,005, 5,326, 882 and a PCT application (88 00695) to Bronstein disclose triggerable dioxetanes bearing adamantyl groups substituted with various groups including chlorine, bromine carboxyl, hydroxyl, methoxy and methylene groups. A publication (M. Ryan, J. C. Huang, O. H. Griffith, J. F. Keana, J. J. Volwerk, Anal. Biochem., 214(2), 548–56 (1993)) discloses a phosphodiester-substituted dioxetane which is triggered by the enzyme phospholipase. U.S. Pat. No. 5,132,204 to Urdea discloses dioxetanes which require two different enzymes to sequentially remove two linked protecting groups in order to trigger the chemiluminescent decomposition. U.S. Pat. No. 5,248,618 to Haces discloses dioxetanes which are enzymatically or chemically triggered to unmask a first protecting group generating an intermediate which spontaneously undergoes an intramolecular reaction to split off a second protecting group in order to trigger the chemiluminescent decomposition.

e. Enhanced Chemiluminescence from Dioxetanes in the Presence of Surfactants. Enhancement of chemiluminescence from the enzyme-triggered decomposition of a stable 1,2-dioxetane in the presence of water-soluble substances including an ammonium surfactant and a fluorescer has been reported (A. P. Schaap, H. Akhavan and L. J. Romano, Clin. Chem., 35(9), 1863 (1989)). Fluorescent micelles consisting of cetyltrimethylammonium bromide (CTAB) and 5-(N-tetradecanoyl)aminofluorescein capture the intermediate hydroxy-substituted dioxetane and lead to a 400-fold increase in the chemiluminescence quantum yield by virtue of an efficient transfer of energy from the anionic form of the excited state ester to the fluorescein compound within the hydrophobic environment of the micelle.

U.S. Pat. Nos. 4,959,182 and 5,004,565 to Schaap describe additional examples of enhancement of chemiluminescence from chemical and enzymatic triggering of stable dioxetanes in the presence of the quaternary ammonium surfactant CTAB and fluorescers. Fluorescent micelles formed from CTAB and either the fluorescein surfactant described above or 1-hexadecyl-6-hydroxybenzothiazamide enhance chemiluminescence from the base-triggered decomposition of hydroxy- and acetoxy-substituted dioxetanes. It was also reported that CTAB itself can enhance the chemiluminescence of a phosphate-substituted dioxetane.

U.S. Pat. No. 5,145,772 to Voyta discloses enhancement of enzymatically generated chemiluminescence from 1,2-dioxetanes in the presence of polymers with pendant quaternary ammonium groups alone or admixed with fluorescein. Other substances reported to enhance chemiluminescence include globular proteins such as bovine albumin and quaternary ammonium surfactants. Other cationic polymer compounds were of modest effectiveness as chemiluminescence enhancers; nonionic polymeric compounds were generally ineffective and the only anionic polymer significantly decreased light emission. A PCT application WO 94/21821 discloses enhancement from the combination of a polymeric ammonium salt surfactant and an enhancement additive. European Patent Application No. 92113448.2 to Akhavan-Tafti published on Sep. 22, 1993 discloses enhancement of enzymatically generated chemiluminescence from 1,2-dioxetanes in the presence of polyvinyl phosphonium salts and polyvinyl phosphonium salts to which fluorescent energy acceptors are covalently attached. Co-pending application U.S. Ser. No. 08/082,091 to Akhavan-Tafti filed Jun. 24, 1993 discloses enhancement of enzymatically generated chemiluminescence from 1,2-dioxetanes in the presence of dicationic phosphonium salts.

Triggerable stabilized dioxetanes known in the art incorporate a rigid spiro-fused polycyclic substituent or a substituted spiroadamantyl substituent. The ketone starting materials from which these dioxetanes are prepared are relatively expensive and are of limited availability or must be prepared from costly precursors. No examples of stable triggerable dioxetanes bearing two alkyl groups in place of rigid spiro-fused polycyclic organic groups are known. Such triggerable stabilized dioxetanes can be prepared from inexpensive, readily available starting materials and will therefore provide cost advantages facilitating their commercial potential.

OBJECTS

It is an object of the present invention to provide novel dialkyl and aryl OX-substituted triggerable 1,2-dioxetane compounds which are stable at room temperature over an extended period of time. It is also an object of the present invention to provide such stable 1,2-dioxetane compounds which can be triggered to decompose with the generation of chemiluminescence. It is also an object of the present invention to provide such stable 1,2-dioxetane compounds which can be prepared from inexpensive, readily available starting materials. It is an object of the present invention to provide a method and compositions containing a stable 1,2-dioxetane which can be triggered by reagents, including enzymes and other chemicals, to generate chemiluminescence. Further, it is an object of the present invention to provide a method and compositions for additionally enhancing the chemiluminescence through the use of enhancer substances. Further the present invention relates to a method and compositions for the detection of enzymes, and for use in immunoassays and the detection of enzyme-linked nucleic acids, antibodies and antigens such as are generally known in the art. Further, it is an object of the present invention to provide a method and compositions for chemical lighting applications.

IN THE DRAWINGS

Figure 3:
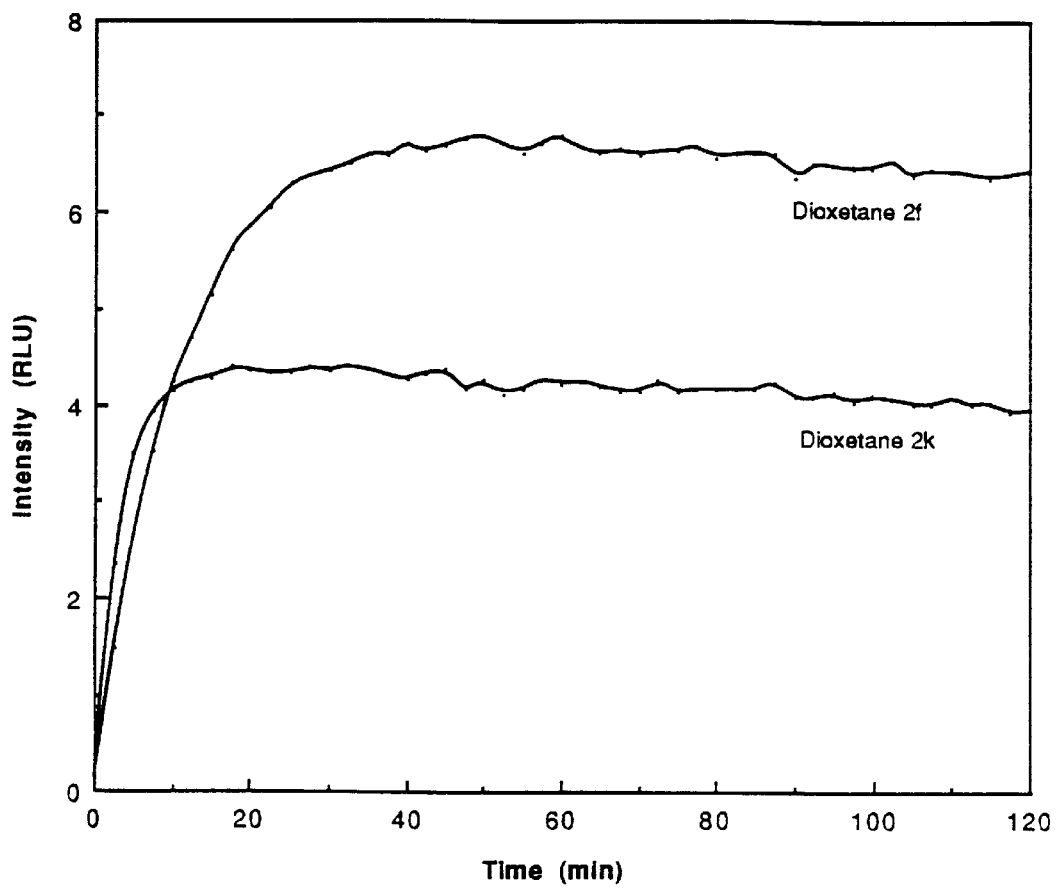

FIG. 3 is a graph showing a comparison of the time profile of the chemiluminescence intensity emitted by 100 $\mu$L of solutions containing either dioxetane 2f of the present invention or 2k (LUMIGEN PPD, Lumigen, Inc., Southfield, Mich.) triggered at 37° C. by addition of $1.12 \times 10^{-17}$ mol of AP. The reagents consist of 1) a 0.33 mM solution of dioxetane 2f in 0.2 M 2-amino-2-methyl-1-propanol buffer, pH 9.6, and 2) a 0.33 mM solution of dioxetane 2k in 0.2 M 2-amino-2-methyl-1-propanol buffer, pH 9.6. Use of dioxetane 2f of the present invention advantageously achieves a higher maximum intensity compared to dioxetane 2k.

Figure 4:
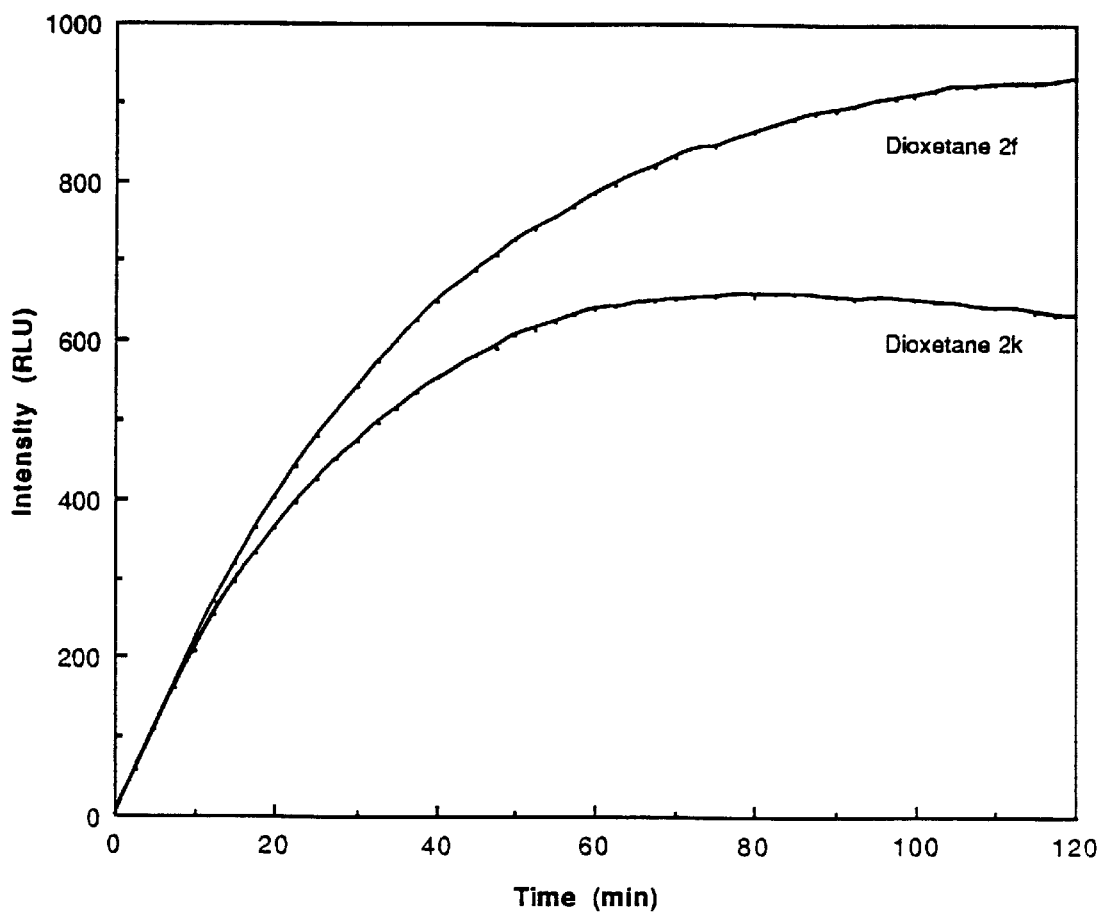

FIG. 4 is a graph showing a comparison of the time profile of the chemiluminescence intensity emitted by 100 $\mu$L of solutions containing either dioxetane 2f or 2k triggered at 37° C. by addition of $1.12 \times 10^{-17}$ mol of AP. The reagents consist of 1) a 0.33 mM solution of dioxetane 2f in 0.2 M 2-amino-2-methyl-1-propanol buffer, pH 9.6 containing 1.0 mg/mL of the enhancer 1-(tri-n-octylphosphoniummethyl)-4-(tri-n-butylphosphoniummethyl)benzene dichloride (Enhancer A), and 2) a 0.33 mM solution of dioxetane 2k in 0.2 M 2-amino-2-methyl-1-propanol buffer, pH 9.6 containing 1.0 mg/mL of the same enhancer. Use of dioxetane 2f of the present invention advantageously achieves higher light intensities at all time points compared to dioxetane 2k.

Figure 5:
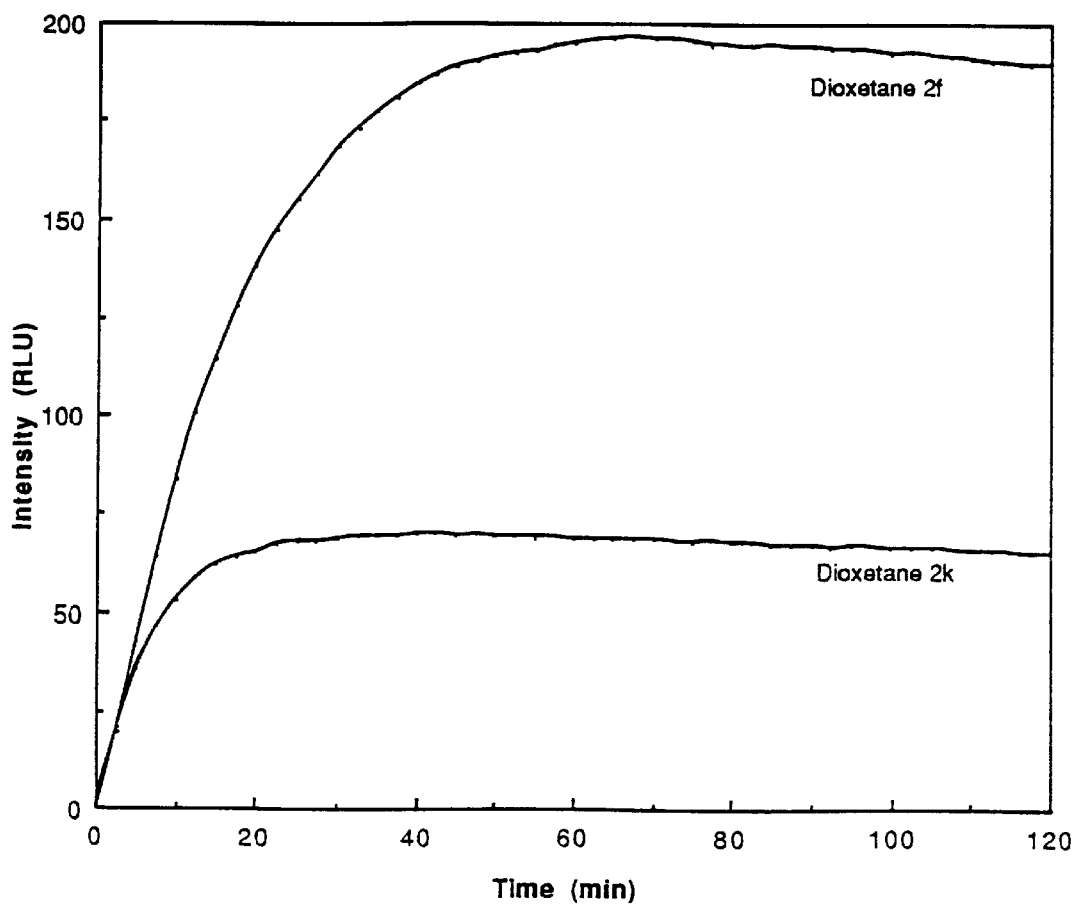

FIG. 5 is a graph showing a comparison of the time profile of the chemiluminescence intensity emitted by 100 μL of another pair of solutions containing either dioxetane 2f or 2k triggered at 37° C. by addition of $1.12 \times 10^{-17}$ mol of AP. The reagents consist of 1) a 0.33 mM solution of dioxetane 2f in 0.2 M 2-amino-2-methyl-1-propanol buffer, pH 9.6 containing 0.5 mg/mL of polyvinylbenzyltributylphosphonium chloride (Enhancer B) and 2) a 0.33 mM solution of dioxetane 2k in 0.2 M 2-amino-2-methyl-1-propanol buffer, pH 9.6 containing 0.5 mg/mL of the same enhancer. The preparation of Enhancer B is described in European Patent Application 561,033 published Sep. 22, 1993. Use of dioxetane 2f of the present invention advantageously achieves higher light intensities at all time points compared to dioxetane 2k.

Figure 6:
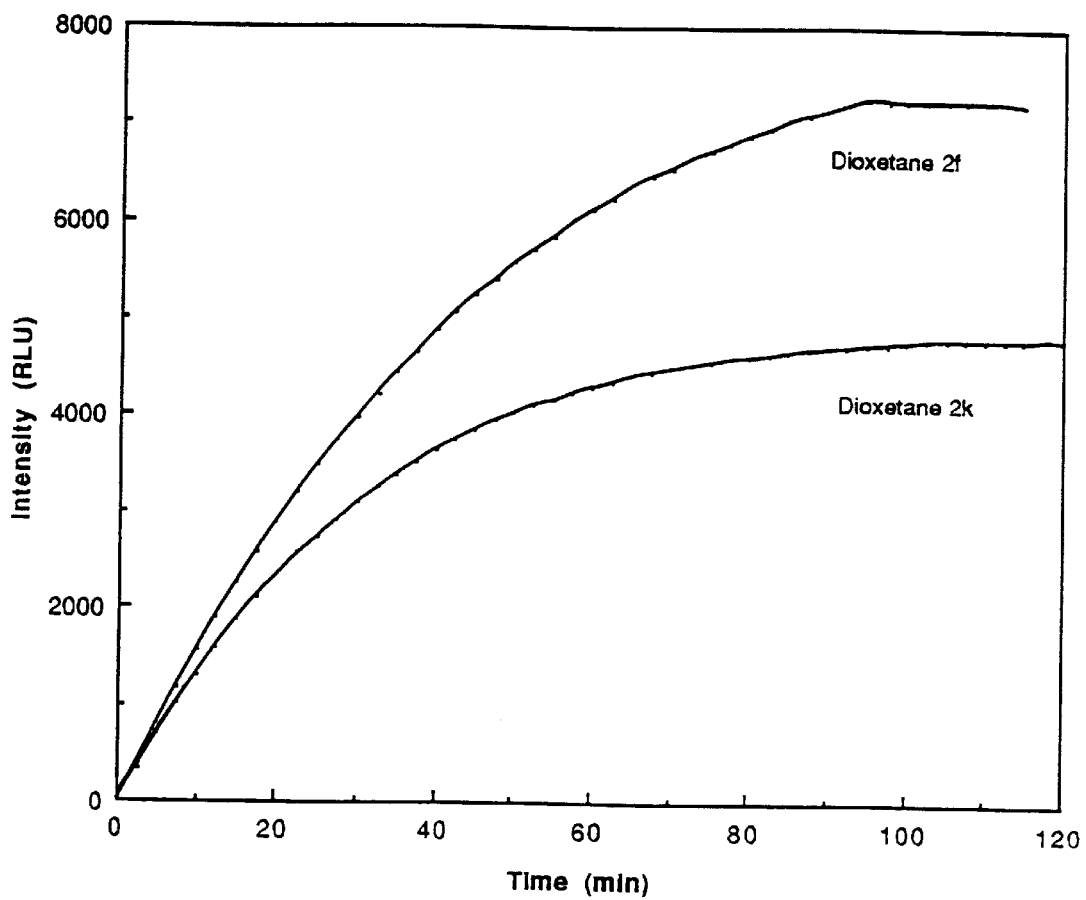

FIG. 6 is a graph showing a comparison of the time profile of the chemiluminescence intensity emitted by 100 μL of another pair of solutions containing either dioxetane 2f or 2k triggered at 37° C. by addition of $1.12 \times 10^{-17}$ mol of AP. The reagents consist of 1) a 0.33 mM solution of dioxetane 2f in 0.2 M 2-amino-2-methyl-1-propanol buffer, pH 9.6 containing 0.5 mg/mL of polyvinylbenzyltributylphosphonium chloride co-polyvinylbenzyltrioctylphosphonium chloride (containing a 3:1 ratio of tributyl:trioctyl groups) (Enhancer C) and 2) a 0.33 mM solution of dioxetane 2k in 0.2 M 2-amino-2-methyl-1-propanol buffer, pH 9.6 containing 0.5 mg/mL of the same enhancer. The preparation of Enhancer C is described in European Patent Application 561,033. Use of dioxetane 2f of the present invention advantageously achieves higher light intensities at all time points compared to dioxetane 2k.

Figure 7:
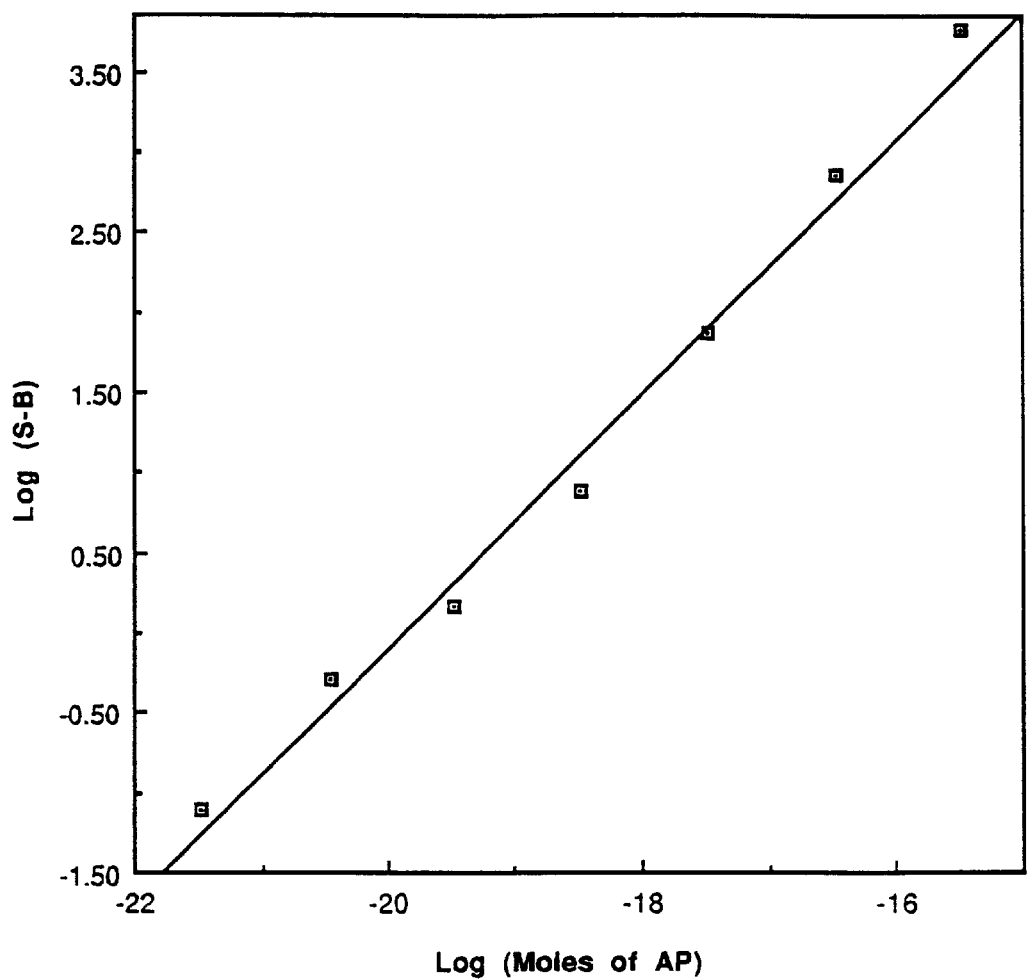

FIG. 7 is a graph relating the maximum chemiluminescence intensity emitted by 100 μL of a reagent containing dioxetane 2f triggered at 37° C. to the amount of AP. Chemiluminescence emission was initiated at 37° C. by addition of 3 μL of solutions of AP containing between $3.36 \times 10^{-16}$ mol and $3.36 \times 10^{-22}$ of enzyme to 100 μL of a 0.33 mM solution of dioxetane 2f in 2-amino-2-methyl-1-propanol buffer, 0.2 M (pH 9.6) containing 1.0 mg/mL of Enhancer A. The term S-B refers to the chemiluminescence signal (S) in Relative Light Units (RLU) in the presence of AP corrected for background chemiluminescence (B) in the absence of AP. The graph shows the linear detection of alkaline phosphatase. The calculated detection limit (twice the standard deviation of the background) was determined to be $1.4 \times 10^{-22}$ mol or less than 100 molecules of alkaline phosphatase under these conditions.

Figure 8:
Figure 8:
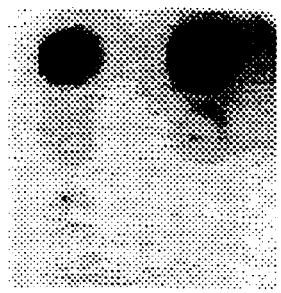

FIGS. 8A and 8B are digitally scanned images of an X-ray film from an experiment detecting alkaline phosphatase on a membrane with chemiluminescence. Solutions of alkaline phosphatase in water containing from $1.1 \times 10^{-15}$ to $1.1 \times 10^{-18}$ mol were applied to identical nylon membranes (Micron Separations Inc., Westboro, Mass.). The membranes were air dried for 5 min and soaked briefly with a reagent containing 1 mg/mL of Enhancer A in 0.2 M 2-amino-2-methyl-1-propanol buffer, pH 9.6 containing 0.88 mM MgCl and either 0.33 mM dioxetane 2f or 0.33 mM dioxetane 2k. The membrane was placed between transparent plastic sheets and exposed to X-ray film (Kodak X-OMAT AR, Rochester, N.Y.). In a comparison of the two reagents, the light produced using dioxetane 2f of the present invention led equivalent images and detection sensitivity. These results illustrate the performance of dioxetane 2f which is to be expected in Western blotting, Southern blotting, DNA fingerprinting and other blotting applications.

DESCRIPTION OF THE PREFERRED EMBODIMENTS

The present invention relates to compositions containing a stable 1,2-dioxetane which can be triggered by reagents, including enzymes and other chemicals, to generate chemiluminescence. Stable dioxetanes useful in practicing the present invention may be of the formula:

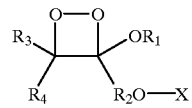

wherein $R_3$ and $R_4$ are nonspirofused organic groups, wherein $R_1$ is an organic group which may be combined with $R_2$ and wherein $R_2$ represents an aryl group substituted with an X-oxy group which forms an unstable oxide intermediate dioxetane compound when triggered to remove a chemically labile group X by a reagent, including enzymes and other chemicals. The unstable oxide intermediate dioxetane decomposes and releases electronic energy to form light and two carbonyl containing compounds of the formula

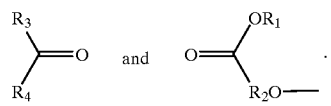

A preferred method of practicing the present invention uses a stable dioxetane of the formula:

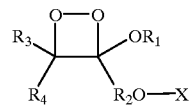

wherein $R_1$ is selected from alkyl, cycloalkyl and aryl groups containing 1 to 12 carbon atoms which may additionally contain heteroatoms, $R_3$ and $R_4$ are selected from branched chain alkyl and cycloalkyl groups containing 3 to 8 carbon atoms and may additionally contain heteroatoms and which provide thermal stability, and wherein $R_2$ is selected from aryl, biaryl, heteroaryl, fused ring polycyclic aryl or heteroaryl groups which can be substituted or unsubstituted and wherein OX is an X-oxy group which forms an unstable oxide intermediate dioxetane compound when triggered to remove a chemically labile group X by a reagent including enzymes and other chemicals.

The stable 1,2-dioxetane compounds have relatively long half-lives at room temperature (20–30° C.) even though they can be triggered by chemical reagents. Previous examples of stable, triggerable 1,2-dioxetanes all made use of rigid spiro-fused polycyclic alkyl groups such as adamantyl and substituted adamantyl to confer thermal stability. It has now been discovered that 1,2-dioxetanes bearing a wider range of substituents corresponding to $R_3$ and $R_4$ in the structure above also exhibit substantial thermal stability at room temperature. Dioxetane compounds substituted with alkyl groups containing as few as 3 carbons (as substituents $R_3$ and $R_4$ in the structure above) have half-lives of approximately one year at room temperature and several years at 4° C. $R_3$ and $R_4$ groups whose carbon atom attached to the dioxetane ring carbon is substituted with zero or one hydrogen atoms (e.g. isopropyl, sec-butyl, t-butyl, cycloalkyl) provide enough thermal stability to the dioxetane compounds to render them useful for practical applications. $R_3$ and $R_4$ groups which are linked to the dioxetane ring through a $CH_2$ group but which are otherwise bulky, for example a neo-pentyl group, are considered to be within the scope of the invention. Further, these dioxetanes can be triggered by the removal of an X group to decompose with emission of light. The degree of rate enhancement upon triggering depends on such factors as the lability of the X group, the amount of the triggering reagent, choice of solvent, pH and temperature. By selecting appropriate conditions, a factor of $10^6$ or greater rate enhancement can be achieved.

The present invention relates to a process using readily available or inexpensive starting materials for preparing a stable 1,2-dioxetane of the formula:

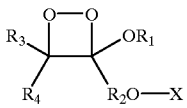

wherein $R_3$ and $R_4$ are nonspirofused organic groups, wherein $R_1$ is an organic group which may be combined with $R_2$ and wherein $R_2$ represents an aryl group substituted with an X-oxy group by addition of oxygen to the appropriate alkene. An unexpected finding of the present invention is that the alkenes reported here readily undergo photochemical addition of a molecule of oxygen (as singlet oxygen $^1O_2$) to produce the corresponding 1,2-dioxetane. It is well known in the literature that alkenes bearing allylic hydrogens may preferentially undergo addition of singlet oxygen by a different reaction path to produce an allylic hydro-peroxide, dioxetane formation is a minor process at most.

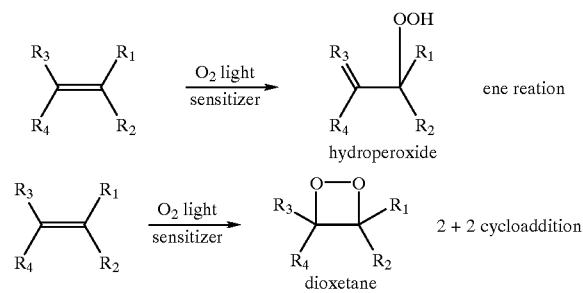

The requisite alkene compounds are synthesized through coupling arylcarboylate esters substituted with an X-oxy group and dialkyl ketones of the formula shown below:

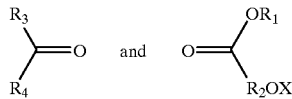

in the presence of lithium aluminum hydride, other metal hydride, zinc metal or zinc-copper couple in a polar aprotic organic solvent, preferably tetrahydrofuran, with a transition metal halide salt, preferably a titanium chloride compound, and a tertiary amine base. The reaction is generally conducted in refluxing tetrahydrofuran and usually goes to completion in about 2 to 24 hours. A significant advantage of the present process is the ability to conduct the reaction on a large scale due to the availability of the ketone starting materials in large quantity. Triggerable dioxetanes in commercial use are prepared from adamantanone or a substituted adamantanone compound. Adamantanone is relatively costly. Substituted adamantanones are even more expensive and of more limited supply. In comparison to the preparation of adamantanone, which involves a laborious procedure involving large quantitities of dangerous oxidizing materials, alkyl and cycloalkyl ketones are readily prepared in large quantities by standard techniques. Another advantage is the reduced cost of certain of the ketone starting materials. Diisopropyl ketone, for example, is between 15 and 20 times less expensive than adamantanone on a molar basis.

The triggering reagent may be a chemical which requires 1 equivalent ($F^-$) or a catalyst such as an enzyme wherein only a small amount is used. Electron donors, organic and inorganic bases, nucleophilic reagents and reducing agents can be used to remove X. The triggering reagent may also be an enzyme selected from but not limited to phosphatase enzymes, esterase enzymes, cholinesterase enzymes, hydrolytic enzymes such as α- and β-galactosidase, α- and β-glucosidase, glucuronidase, trypsin and chymotrypsin.

The OX group may include, without limitation, hydroxyl, $OOCR_6$ wherein $R_6$ is an alkyl or aryl group containing 2 to 20 carbon atoms either of which may contain heteroatoms, trialkylsilyloxy, triarylsilyloxy, aryldialkylsilyloxy, $OPO_3^{-2}$ salt, $OSO_3^-$ salt, β-D-galactosidoxy and β-D-glucuronidyloxy groups.

The present invention relates to a method for generating light which comprises providing a chemical reagent and a stable 1,2-dioxetane of the formula:

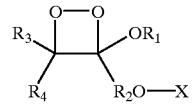

wherein $R_3$ and $R_4$ are organic groups which are selected from lower alkyl or cycloalkyl containing 3 to 8 carbon atoms and which provide thermal stability, wherein $R_1$ is an organic group which may be combined with $R_2$ and wherein $R_2$ represents an aryl group substituted with an X-oxy group which forms an unstable oxide intermediate dioxetane compound when triggered to remove a chemically labile group X by a reagent including enzymes and other chemicals wherein the unstable oxide intermediate dioxetane decomposes and releases electronic energy to form light and two carbonyl containing compounds of the formula:

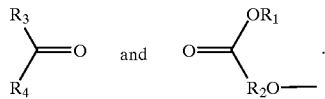

The present invention also relates to a method for detecting triggering reagents selected from chemical reagents including enzymes. In this instance the dioxetane is used as the reagent.

Further the present invention relates to a method and compositions for the detection of enzymes, in immunoassays, e. g. ELISA and the detection of enzyme-linked DNA or RNA probes. Detection of the light emitted may be readily performed using a luminometer, X-ray film or with a camera and photographic film.

EXAMPLES

Nuclear magnetic resonance (NMR) spectra were obtained on a GE QE300 or a Varian Gemini 300 spectrometer as solutions in CDCl₃ with tetramethylsilane as internal standard or as solutions in CD₃OD or D₂O. Mass spectra were obtained on an AEI MS-90™ spectrometer.

Example 1

Synthesis of 1-(3-t-Butyldimethylsilyloxyphenyl)-2,2-diisopropyl-1-methoxyethene (1a)

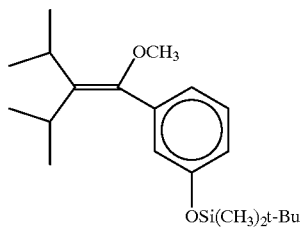

A three neck flask was purged with argon and charged with 100 mL of anhydrous tetrahydrofuran (THF). The flask was cooled in an ice bath and titanium trichloride (18 g) was added with stirring. Lithium aluminum hydride (2.2 g) was added in small portions causing a brief exothermic reaction. After all of the lithium aluminum hydride was added the cooling bath was removed and triethylamine (16 ml) was added. The black mixture was refluxed for one hour under argon. A solution of 2,4-dimethyl-3-propanone (3.86 g) and methyl 3-t-butyl-dimethylsilyloxybenzoate (3.00 g) in 10 mL of dry THF was added dropwise over 2 hours. Reaction progress was monitored by TLC on silica plates eluting with 4% ethyl acetate/hexane. The crude reaction mixture was cooled to room temperature and diluted with hexane and decanted. The residue was washed several times using a total of ca. 700 mL of hexane. The combined hexane solutions were filtered and evaporated leaving an oil which was purified by column chromatography on silica gel, eluting with hexane yielding 2.12 g (54%) of 1a: ¹H NMR (CDCl₃) δ 7.3–6.7 (m, 4H), 3.18 (s, 3H), 2.45 (sept, 1H, J=7.2 Hz), 2.31 (sept, 1H, J=7.2 Hz), 1.24 (d, 6H, J=7.2 Hz), 0.99 (s, 3H), 0.91 (d, 6H, J=7.2 Hz), 0.19 (s, 3H); ¹³C NMR (CDCl₃) δ 128.76, 122.84, 121.46, 119.28, 56.06, 30.32, 26.54, 25.56, 21.91, 20.86, −4.58; Mass spectrum (m/z): 348, 333, 306; exact mass, calc'd. 348.2484, found 348.2479.

Example 2

Synthesis of 2,2-Diisopropyl-1-(3-hydroxyphenyl)-1-methoxyethene (1b)

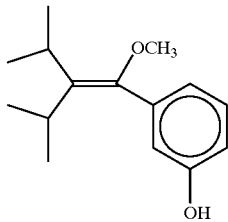

To a solution of 0.97 g (2.78 mmol) of alkene 1a in 30 ml of dry THF was added 0.81 g (1.1 eq.) of tetra-n-butylammonium fluoride. After stirring for one hour TLC (silica, 20% ethyl acetate/hexane) showed complete conversion of starting material to a new compound. The THF was evaporated and the residue dissolved in ethyl acetate. The ethyl acetate solution was extracted four times with water and dried. Silica gel (2 g) was added and the solvent evaporated. The material was purified by column chromatography on silica gel, eluting with 10–20% ethyl acetate/hexane yielding 0.568 g (87%) of 1b: ¹H NMR (CDCl₃) δ 7.5–6.5 (m, 4H), 4.91 (s, 1H), 3.20 (s, 3H), 2.47 (sept, 1H), 2.33 (sept, 1H), 1.25 (d, 6H), 0.92 (d, 6H); ¹³C NMR (CDCl₃) δ 129.25, 124.98, 122.60, 116.54, 114.98, 114.56, 56.38, 30.52, 26.80, 22.11, 21.08; Mass spectrum (m/z): 234, 219, 191; exact mass, calc'd. 234.1620, found 234.1620.

Example 3

Synthesis of 1-(3-Acetoxyphenyl)-2,2-diisopropyl-1-methoxyethene (1c).

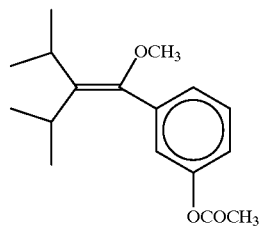

Alkene 1b (200 mg, 0.85 mmol) was dissolved in 20 mL of dry methylene chloride with 0.3 mL of anhydrous pyridine. The flask was purged with argon and cooled in an ice bath. Acetyl chloride (0.115 g, 1.47 mmol) in 5 mL of dry methylene chloride was added dropwise over one hour. TLC analysis (silica, 20% ethyl acetate/hexane) indicated the reaction to be complete after 2.5 hours of stirring at 0° C. The solvents were evaporated and the residue dissolved in ethyl acetate. The solution was washed four times with water, dried over MgSO₄ and evaporated. The residue was purified by column chromatography on silica gel, eluting with 10–20% ethyl acetate/hexane yielding 220 mg (93%) of 1c: ¹H NMR (CDCl₃) δ 7.37–6.99 (m, 4H), 3.19 (s, 3H), 2.47 (sept, 1H, J=6.9 Hz), 2.33 (sept, 1H, J=6.9 Hz), 2.29 (s, 3H), 1.24 (d, 6H, J=6.9 Hz), 0.93 (d, 6H, J=6.9 Hz); ¹³C NMR (CDCl₃) δ 169.46, 150.62, 149.03, 139.02, 133.64, 128.95, 127.24, 122.89, 120.72, 56.50, 30.49, 26.98, 22.06, 21.25, 21.05.

Example 4

Synthesis of 1-(3-Benzoyloxyphenyl)-2,2-diisopropyl-1-methoxyethene (1d)

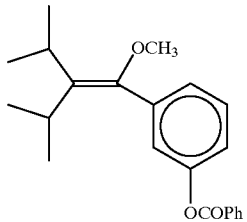

Alkene 1b (4.5 g, 1.9 mmol) was dissolved in 50 mL of dry CH₂Cl₂ with 5.3 mL of anhydrous triethylamine. The flask was purged with argon and cooled in an ice bath. Benzoyl chloride (4.05 g, 2.9 mmol) was added dropwise. The cooling bath was removed and stirring continued for 1 hour at room temperature. The mixture was filtered and the solution was washed with water, dried over MgSO$_4$ and evaporated. The residue was suspended in hexane, the solid filtered away and the solution evaporated. The residue was purified by column chromatography on silica gel, eluting with 1% ethyl acetate in hexane yielding 3.7 g of dioxetane 1d: $^1$H NMR (CDCl$_3$) δ 8.25–7.05 (m, 9H), 3.25 (s, 1H), 2.54 (sept, 1H, J=6.9 Hz), 2.40 (sept, 1H, J=6.9 Hz), 2.29 (s, 3H), 1.26 (d, 6H, J=6.9 Hz), 0.95 (d, 6H, J=6.9 Hz).

Example 5

Synthesis of 1-(3-Pivaloyloxyphenyl)-2,2-diisopropyl-1-methoxyethene (1e)

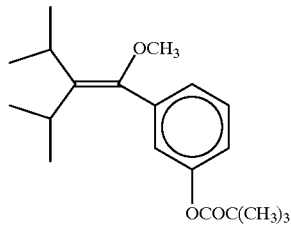

Alkene 1b (2 g, 8.6 mmol) was dissolved in 50 mL of dry CH$_2$Cl$_2$ with 2.4 mL of anhydrous triethylamine. The flask was purged with argon and cooled in an ice bath. Pivaloyl chloride (1.6 g, 2 eq.) was added dropwise over one hour. The cooling bath was removed and stirring continued for 3 hours at room temperature. The solution was washed with aq. K$_2$CO$_3$ and then water, dried over MgSO$_4$ and evaporated. The residue was purified by column chromatography on silica gel, eluting with 5% triethylamine in hexane yielding 1.95 g of dioxetane 1e: $^1$H NMR (CDCl$_3$) δ 7.34–6.98 (m, 4H), 3.198 (s, 3H), 2.47 (sept, 1H), 2.33 (sept, 1H), 1.36 (s, 9H), 1.24 (d, 6H, J=6.9 Hz), 0.92 (d, 6H, J=6.9 Hz).

Example 6

Synthesis of 2,2-Diisopropyl-1-methoxy-1(3-phosphoryloxyphenyl)ethene, disodium salt (1f)

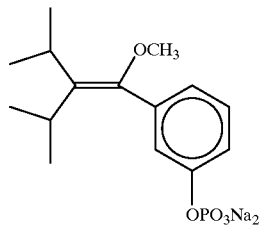

(a) A solution of 9 mL of dry CH$_2$Cl$_2$ and 0.7 mL of anhydrous pyridine (8.7 mmol) was purged with argon and cooled in an ice bath. Phosphorus oxychloride (0.40 g, 2.6 mmol) was added followed after 5 min by a solution of alkene 1b (209 mg, 0.87 mmol) in 0.4 mL of pyridine. The solution was stirred at room temperature for 1 hour. TLC analysis (silica, 30% ethyl acetate/hexane) indicated the reaction to be complete. The solvents were evaporated and the residue taken on to the nest step.

(b) The product from step (a) was dissolved in CH$_2$Cl$_2$ and 0.7 mL of pyridine added. The solution was cooled in an ice bath and treated with 618 mg of 2-cyanoethanol (8.7 mmol). The ice bath was removed and stirring continued at room temperature for two hours. The mixture was then concentrated and the residue was purified by column chromatography on silica gel, eluting with a gradient of 50% ethyl acetate in hexane to 100% ethyl acetate yielding of the bis(cyanoethyl phosphate) $^1$H NMR (CDCl$_3$) δ 0.934 (d, 6H, J=9 Hz), 1.235 (d, 6H, J=9 Hz), 2.28–2.45 (m, 2H), 2.76–2.82 (m, 4H), 3.18 (s, 1H), 4.31–4.47 (m, 4H), 7.11–7.38 (m, 4H).

(c) The bis(cyanoethyl phosphate) alkene (420 mg) was dissolved in 4 mL of acetone. Sodium hydroxide (65 mg) was dissolved in 1 mL of water and added to the acetone solution which was then stirred over night. The precipitate was collected and dried to a white powder. $^1$H NMR (D$_2$O) δ 0.907 (s, 3H), 0.929 (s, 3H), 1.20 (s, 3H), 1.22 (s, 3H), 2.35–2.46 (m, 2H), 3.23 (s, 1H), 6.96–7.37 (m, 4H); $^{13}$C NMR (D$_2$O) δ 155.15 (d), 149.56, 137.84, 136.08, 129.71, 124.55, 122.33 (d), 120.48, 57.16, 31.27, 27.21, 22.59, 21.10; $^{31}$P NMR (D$_2$O) (rel. To ext. H$_3$PO$_4$) δ 0.345.

Example 7

Synthesis of 1-(3-t-Butyldimethylsilyloxyphenyl)-2,2-dicyclopropyl-1-methoxyethene (1a)

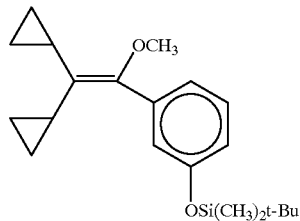

A three neck flask was purged with argon and charged with 50 mL of anhydrous THF. The flask was cooled in an ice bath and titanium trichloride (11.6 g) was added with stirring. Lithium aluminum hydride (1.4 g) was added in small portions causing a brief exothermic reaction. While the lithium aluminum hydride was being added, an additional 20 mL portion of anhydrous THF was added to aid stirring. The cooling bath was removed when the addition was complete and the black mixture was brought to reflux. Triethylamine (10.5 ml) was added and the black mixture was refluxed for one hour under argon. A solution of dicyclopropyl ketone (2.61 g) and methyl 3-t-butyldimethylsilyloxybenzoate (2.00 g) in 20 mL of dry THF was added dropwise over 75 min. The reaction was judged complete after an additional 1 hour reflux period as monitored by TLC on silica plates eluting with 5% ethyl acetate/hexane. The crude reaction mixture was cooled to room temperature and extracted with four 400 mL portions of hexane. The combined hexane solutions were filtered and evaporated leaving 1.42 g of a yellow oil which was purified by column chromatography on silica gel, eluting first with hexane and then with 20% ethyl acetate/hexane to elute the product alkene 1a. Further purification was achieved by preparative TLC on silica eluting with 5% ethyl acetate/hexane. $^1$H NMR (CDCl$_3$) δ 7.3–6.7 (m, 4H), 3.36 (s, 3H), 1.80 (m, 1H), 1.13 (m, 1H), 0.988 (s, 9H), 0.78–0.67 (m, 4H), 0.43–0.37 (m, 2H), 0.19 (s, 6H), 0.11–0.05 (m, 2H).

Example 8

Synthesis of 1-(3-t-Butyldimethylsilyloxyphenyl)-2,2-dicyclohexyl-1-methoxyethene (1h)

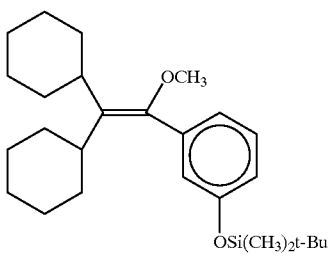

A mixture of 4.3 g of methyl 3-t-butyldimethylsilyloxybenzoate and 9.5 g of dicyclohexyl ketone in dry THF were coupled according to the procedure of Example 5 using the Ti reagent made from 25 g of $TiCl_3$, 3.0 g of $LiAlH_4$ and 16.4 g of triethylamine in 150 mL of dry THF. The crude product mixture (10 g) obtained after hexane extraction was purified by column chromatography on silica gel, eluting first with hexane, followed by 1% ethyl acetate/hexane and then with 3% ethyl acetate/hexane. The yield was 3.5 g (51%) of alkene 1e: $^1$H NMR ($CDCl_3$) δ 7.22–7.16 (m, 1H), 6.85–6.72 (m, 3H), 3.155 (s, 3H), 2.05–0.86 (m, 22H), 0.995 (s, 9H), 0.21 (s, 6H).

Example 9

Synthesis of 2,2-Dicyclohexyl-1-(3-hydroxyphenyl)-1-methoxyethene (1i)

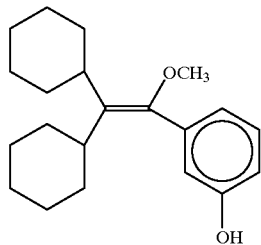

To a solution of 0.7 g of alkene 1f in dry THF was added 0.62 g (1.2 eq.) of tetra-n-butylammonium fluoride dropwise. After stirring for one hour TLC (silica, 20% ethyl acetate/hexane) showed complete conversion of starting material to a new compound. The THF was evaporated and the residue dissolved in ethyl acetate. The ethyl acetate solution was extracted with water and dried over $MgSO_4$. The material was purified by column chromatography on silica gel, eluting with 0–10% ethyl acetate/hexane yielding 0.46 g (92%) of 1f. The alkene was further purified by crystallization in benzene/hexane (1:6) at 4° C.: $^1$H NMR ($CDCl_3$) δ 7.20–6.72 (m, 4H), 4.72 (s, 1H), 3.174 (s, 3H), 2.06–1.04 (m, 22H); $^{13}$C NMR ($CDCl_3$) δ 155.19, 138.20, 131.97, 129.05, 122.50, 116.36, 114.39, 56.48, 41.51, 39.34, 31.40, 30.92, 27.50, 26.37, 26.25, 25.99; Mass spectrum (m/z): 314, 231, 121; exact mass, calc'd. 314.2246, found 314.2246.

TABLE 1

Dioxetane Compounds

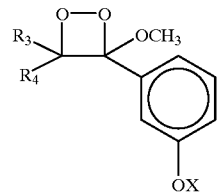

| Dioxetane | $R_3$ | $R_4$ | X |
|---|---|---|---|
| 2a | $CH(CH_3)_2$ | $CH(CH_3)_2$ | $Si(CH_3)_2$t-Bu |
| 2b | $CH(CH_3)_2$ | $CH(CH_3)_2$ | H |
| 2c | $CH(CH_3)_2$ | $CH(CH_3)_2$ | $COCH_3$ |
| 2d | $CH(CH_3)_2$ | $CH(CH_3)_2$ | COPh |
| 2e | $CH(CH_3)_2$ | $CH(CH_3)_2$ | $COC(CH_3)_3$ |
| 2f | $CH(CH_3)_2$ | $CH(CH_3)_2$ | $PO_3Na_2$ |
| 2g | c-$C_3H_5$ | c-$C_3H_5$ | $Si(CH_3)_2$t-Bu |
| 2h | c-$C_6H_{11}$ | c-$C_6H_{11}$ | $Si(CH_3)_2$t-Bu |
| 2i | c-$C_6H_{11}$ | c-$C_6H_{11}$ | H |
| 2j | - adamantyl - | | $Si(CH_3)_2$t-Bu |
| 2k | - adamantyl - | | $PO_3Na_2$ |

Example 10

Synthesis of 1,2-Dioxetanes

Photooxygenation procedure. Method A. Typically a 100 mg sample of the alkene was dissolved in 20 mL of a 1:1 mixture of methanol and methylene chloride in a photooxygenation tube. Approximately 200 mg of polystyrene-bound Rose Bengal was added and an oxygen bubbler connected. Oxygen was passed slowly through the apparatus while immersed in a half-silvered Dewar flask containing either Dry Ice/2-propanol or ice water. The sample was irradiated with a 400 W sodium lamp (GE Lucalox) through a film of 5 mil Kapton (DuPont, Wilmington, Del.) as UV cutoff filter while continuously bubbling oxygen. Progress of the reaction was monitored by TLC or $^1$H NMR. The dioxetane compound was isolated by filtering off the polymer-bound sensitizer and evaporating the solvent at room temperature. Further purification could be achieved by column chromatography on silica gel or crystallization from a suitable solvent as necessary.

Method B. Alternatively, methylene blue was used in some cases as photosensitizer. Approximately 100 mg was dissolved in 10 mL of the reaction solvent and irradiation proceeded as described above. The dioxetanes prepared in this manner were purified by column chromatography on silica gel.

Example 11

Synthesis of 4-(3-t-Butyldimethylsilyloxyphenyl)-3,3-diisopropyl-4-methoxy-1,2-dioxetane (2a)

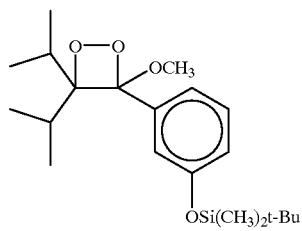

A 102.8 mg sample of the alkene was photooxygenated for a total of 9 hours by method B at −78° C. The solvent was evaporated and the mixture purified by preparative TLC using 4% ethyl acetate/hexane to elute the plate. The yield of dioxetane 2a was 55.9 mg (50%). $^1$H NMR (CDCl$_3$) δ 7.6–6.7 (m, 4H), 3.14 (s, 3H), 2.61 (sept, 1H), 2.46 (sept, 1H), 1.30 (d, 1H), 1.18 (d, 1H), 1.00 (s, 3H), 0.92 (d, 1H), 0.46 (d, 1H), 0.20 (s, 3H); $^{13}$C NMR (CDCl$_3$) δ 155.88, 137.07, 129.41, 114.526, 98.57, 49.46, 33.51, 29.24, 25.79, 19.43, 18.51, 17.29, 16.69, −4.32.

Example 12

Synthesis of 3,3-Diisopropyl-4-(3-hydroxyphenyl)-4-methoxy-1,2-dioxetane (2b)

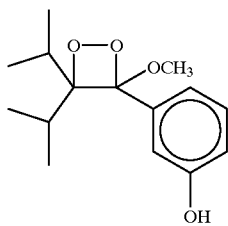

Alkene 1b (83.2 mg) was photooxygenated for a total of 3 hours by method B at −78° C. The solvent was evaporated, the residue dissolved in ethyl acetate and the mixture purified by preparative TLC using 20% ethyl acetate/hexane to elute the plate. The yield of dioxetane 2b was 79 mg (84%). $^1$H NMR (CDCl$_3$) δ 7.4–6.8 (m, 4H), 3.2 (s, 3H), 2.62 (sept, 1H), 2.48 (sept, 1H), 2.08 (s,1H), 1.30 (d, 3H), 1.17 (d, 3H), 0.90 (d, 3H), 0.47 (d, 3H); $^{13}$C NMR (CDCl$_3$) δ 156.00, 137.21, 129.70, 116.41, 114.61, 98.97, 49.58, 33.55, 29.35, 19.46, 18.56, 17.31, 16.65.

Example 13

Synthesis of 4-(3-Acetoxyphenyl)-3,3-diisopropyl-4-methoxy-1,2-dioxetane (2c)

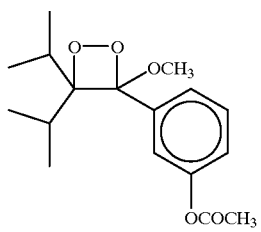

A 63 mg sample of the alkene was photooxygenated for a total of 6.5 hours by method B at −78° C. The solvent was evaporated, the residue dissolved in ethyl acetate and the mixture purified by preparative TLC using 20% ethyl acetate/hexane to elute the plate. The yield of dioxetane 2c was 56 mg (80%). $^1$H NMR (CDCl$_3$) δ 7.37–6.99 (m, 4H), 3.14 (s, 3H), 2.59–2.42 (m, 2H), 2.32 (s, 3H), 1.30 (d, 3H, J=7.2 Hz), 1.17 (d, 3H, J=7.2 Hz), 0.91 (d, 3H, J=7.2 Hz), 0.46 (d, 3H, J=7.2 Hz); $^{13}$C NMR (CDCl$_3$) δ 150.89, 137.34, 129.39, 122.73, 114.07, 98.34, 49.60, 33.54, 29.31, 21.22, 19.44, 18.53, 17.17, 16.59.

Example 14

Synthesis of 4-(3-Benzoyloxyphenyl)-3,3-diisopropyl-4-methoxy-1,2-dioxetane (2d)

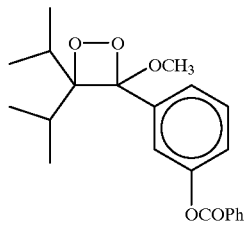

A 3.7 g sample of the alkene was photooxygenated for a total of 19 hours by method B at −78° C. using 500 mL of a 1:1 mixture of acetone and CH$_2$Cl$_2$ and 100 mg of methylene blue. Progress of the reaction was monitored by $^1$H NMR. The solvent was evaporated, the residue dissolved in ethyl acetate and the mixture purified by column chromatography using hexane as eluent. $^1$H NMR (CDCl$_3$) δ 8.22–7.0 (m, 9H), 3.184 (s, 3H), 2.62–2.46 (m, 2H), 1.30 (d, 3H, J=7.2 Hz), 1.20 (d, 3H, J=7.2 Hz), 0.94 (d, 3H, J=7.2 Hz), 0.52 (d, 3H, J=7.2 Hz); $^{13}$C NMR (CDCl$_3$) δ 151.09, 137.32, 133.72, 130.18, 129.33, 128.61, 122.66, 98.24, 49.48, 33.44, 29.22, 19.32, 18.42, 17.11, 16.48.

Example 15

Synthesis of 4-(3-Pivaloyloxyphenyl)-3,3-diisopropyl-4-methoxy-1,2-dioxetane (2e)

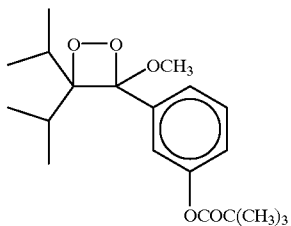

A 1.95 g sample of the alkene was photooxygenated for a total of 2.5 hours by method B at 4° C. using 300 mL of a 1:1 mixture of acetone and CH$_2$Cl$_2$. Progress of the reaction was monitored by $^1$H NMR. The solvent was evaporated, the residue dissolved in ethyl acetate and the mixture purified by column chromatography using hexane as eluent. $^1$H NMR (CDCl$_3$) δ 7.43–7.07 (m, 4H), 3.14 (s, 3H), 2.59–2.42 (m, 2H), 1.37 (s, 9H), 1.31 (d, 3H, J=6.9 Hz), 1.17 (d, 3H, J=6.9 Hz), 0.92 (d, 3H, J=6.9 Hz), 0.47 (d, 3H, J=6.9 Hz)

Example 16

Synthesis of 4-(3-Phosphoryloxyphenyl)-3,3-diisopropyl-4-methoxy-1,2-dioxetane, disodium salt (2f)

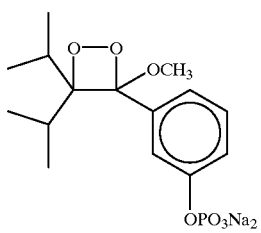

A 64 mg sample of the alkene was photooxygenated for a total of 1.5 hours in 3 mL of D$_2$O at 0° C. according to Method B. The solution was stored at 4° C. to induce crystallization. The white crystals were filtered, washed with acetone and dried. $^1$H NMR (D$_2$O) δ 7.43–7.14 (m, 4H), 3.132 (s, 3H), 2.63–2.53 (m, 2H), 1.225 (d, 3H, J=7.5 Hz), 1.123 (d, 3H, J=7.5 Hz), 0.892 (d, 3H, J=6.6 Hz), 0.475 (d, 3H, J=6.6 Hz); $^{31}$P NMR (D$_2$O) (rel. To ext. H$_3$PO$_4$) δ 0.248.

It should be noted that all other solvent systems used including D$_2$O/p-dioxane, methanol, methanol/CH$_2$Cl$_2$ required reaction times of several hours and led to significant quantities of decomposition products.

Example 17

Synthesis of 4-(3-t-Butyldimethylsilyloxyphenyl)-3,3-dicyclopropyl-4-methoxy-1,2-dioxetane (2a)

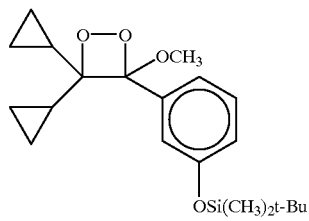

A 25 mg sample of the alkene was photooxygenated for a total of 1 hour by method A at −78° C. $^1$H NMR indicated the solution to contain a 3:1 mixture of dioxetane to alkene and a small amount of the ester decomposition product. Irradiation was stopped at this point and the sensitizer filtered away. The solvent was evaporated and the mixture used as a solution in xylene for kinetic measurements. $^1$H NMR (CDCl$_3$) peaks due to dioxetane: δ 7.6–6.7 (m, 4H), 3.14 (s, 3H), 1.80 (m, 1H), 1.2–1.0 (m, 9H), 0.991 (s, 9H), 0.221 (s, 6H).

Example 18

Synthesis of 4-(3-t-Butyldimethylsilyloxyphenyl)-3,3-dicyclohexyl-4-methoxy-1,2-dioxetane (2h)

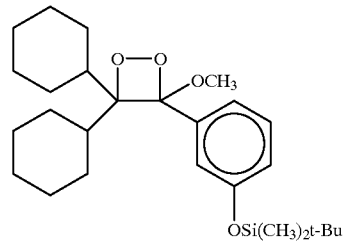

A 2.0 g sample of alkene 1f was photooxygenated for a total of 8.5 hours by method B at −78° C. The solvent was evaporated, the residue dissolved in hexane and filtered. The organic solution was evaporated and the solid residue was purified by column chromatography. The yield of product was 2.0 g (93%). $^1$H NMR (CDCl$_3$) δ 7.26–6.85 (m, 4H), 3.143 (s, 3H), 2.3–0.5 (m, 22H) 0.995 (s, 9H), 0.205 (s, 6H); $^{13}$C NMR (CDCl$_3$) δ 155.57, 136.82, 129.10, 122–121 (several unresolved), 114.56, 104.39, 97.31, 49.49, 45.18, 41.79, 28.71, 28.07, 27.80, 27.17, 26.95, 26.83, 26.74, 26.30, 25.68, 18.24, −4.38.

Example 19

Synthesis of 3,3-Dicyclohexyl-4-(3-hydroxyphenyl)-4-methoxy-1,2-dioxetane (2i)

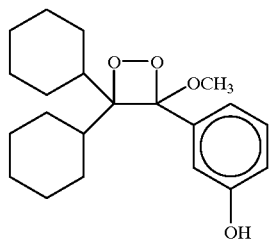

A 150 mg sample of alkene 1g was photooxygenated for a total of 1.5 hours by method B at −78° C. The solvent was evaporated, the residue dissolved in hexane and filtered. The precipitate was washed with 10 ml of 20% ethyl acetate/hexane and the organic solution evaporated. The solid residue was purified by preparative TLC using 20% ethyl acetate/hexane to elute the plate. The yield of product was 120 mg (72%). $^1$H NMR (CDCl$_3$) δ 7.34–6.93 (m, 4H), 5.30 (s, 1H), 3.163 (s, 3H), 2.23–0.56 (m, 22H); $^{13}$C NMR (CDCl$_3$) δ 155.55, 137.02, 129.42, 116.23, 116.12, 114.62, 104.36, 97.88, 49.60, 45.28, 41.78, 28.70, 28.09, 27.75, 27.14, 26.90, 26.86, 26.72, 26.37.

Example 20

Synthesis of 1-(tri-n-octylphosphoniummethyl)-4-(tri-n-butylphosphoniummethyl)benzene dichloride Enhancer A

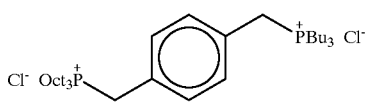

(a) A mixture of tri-n-butylphosphine (7 g, 34.6 mmol) in toluene (50 mL) was added dropwise to a mixture of α,α'-dichloro-p-xylene (12.1 g, 69.2 mmol, 2 eq.) in toluene (200 mL) under argon. The reaction mixture was stirred for 12 hours at room temperature under argon, after which time 4-(chloromethyl)benzyl-tri-n-butylphosphonium chloride had crystallized out of solution. The crystals were filtered and washed with toluene and hexane and air dried: $^1$H NMR (CDCl$_3$) δ 0.92 (t,9H), 1.44 (m, 12H), 2.39 (m, 6H), 4.35–4.40 (d, 2H), 4.56 (s, 2H), 7.36–7.39 (d, 2H), 7.47–7.51 (dd, 2H).

(b) To a mixture of 4-(chloromethyl)benzyl-tri-n-butylphosphonium chloride (3 g, 7.9 mmol) in DMF at room temperature, under argon was added tri-n-octylphosphine (4.39 g, 12 mmol). The reaction mixture was allowed to stir for several days, after which time TLC examination showed the reaction to be complete. The DMF was removed under reduced pressure, the residue washed with hexanes and toluene several times and then dried to give 1-(tri-n-octylphosphoniummethyl)-4-(tri-n-butylphosphoniummethyl)benzene dichloride as white crystals: $^1$H NMR (CDCl$_3$) δ 0.84 (t,9H), 0.89 (t, 9H), 1.22 (br s, 24H), 1.41 (m,24H), 2.34 (m, 12H), 4.35–4.40 (d, 4H), 7.58 (s, 4H); $^{13}$C NMR (CDCl$_3$) δ 13.34, 13.94, 18.33, 18.62, 18.92, 19.21, 21.76, 21.81, 23.58, 23.64, 23.78, 23.98, 26.10, 26.65, 28.86, 30.68, 30.88, 31.53, 129.22, 131.22; $^{31}$P NMR (D$_2$O) δ 31.10. 31.94.

Example 21

Measurement of Chemiluminescence Kinetics

Chemiluminescence intensities and rate measurements were performed using either a Turner Designs (Sunnyvale, Calif.) model TD-20e luminometer or a luminometer built in house (Black Box) which uses a photon counting photomultiplier. Temperature control of samples analyzed in the luminometers was achieved by means of a circulating bath connected to the instrument. Quantitative measurement of light intensities on the Turner luminometer was extended beyond the 10$^4$ linear range of the detector by a neutral density filter. Data collection was controlled by an Apple MacIntosh SE/30 computer using the LUMISOFT data reduction program (Lumigen, Inc., Southfield, Mich.).

Activation energies for thermal decomposition of dioxetanes 2c, h and i were determined by measuring the first order rate constant k for decay of chemiluminescence of dilute solutions in xylene at several temperatures.

TABLE 2

Thermal Stability of Stabilized Dioxetanes

| Dioxetane | Ea (kcal/mol) | log A | t½ 25° C. | t½ 4° C. |
|---|---|---|---|---|
| 2c | 28.1 | 12.85 | 1.2 yr | 43.9 yr |
| 2h | 29.4 | 13.7 | 1.7 yr | 72.3 yr |
| 2i | 28.5 | 13.2 | 1.1 yr | 43.4 yr |

Example 22

Chemiluminescence and Fluorescence Spectra

Figure 1:
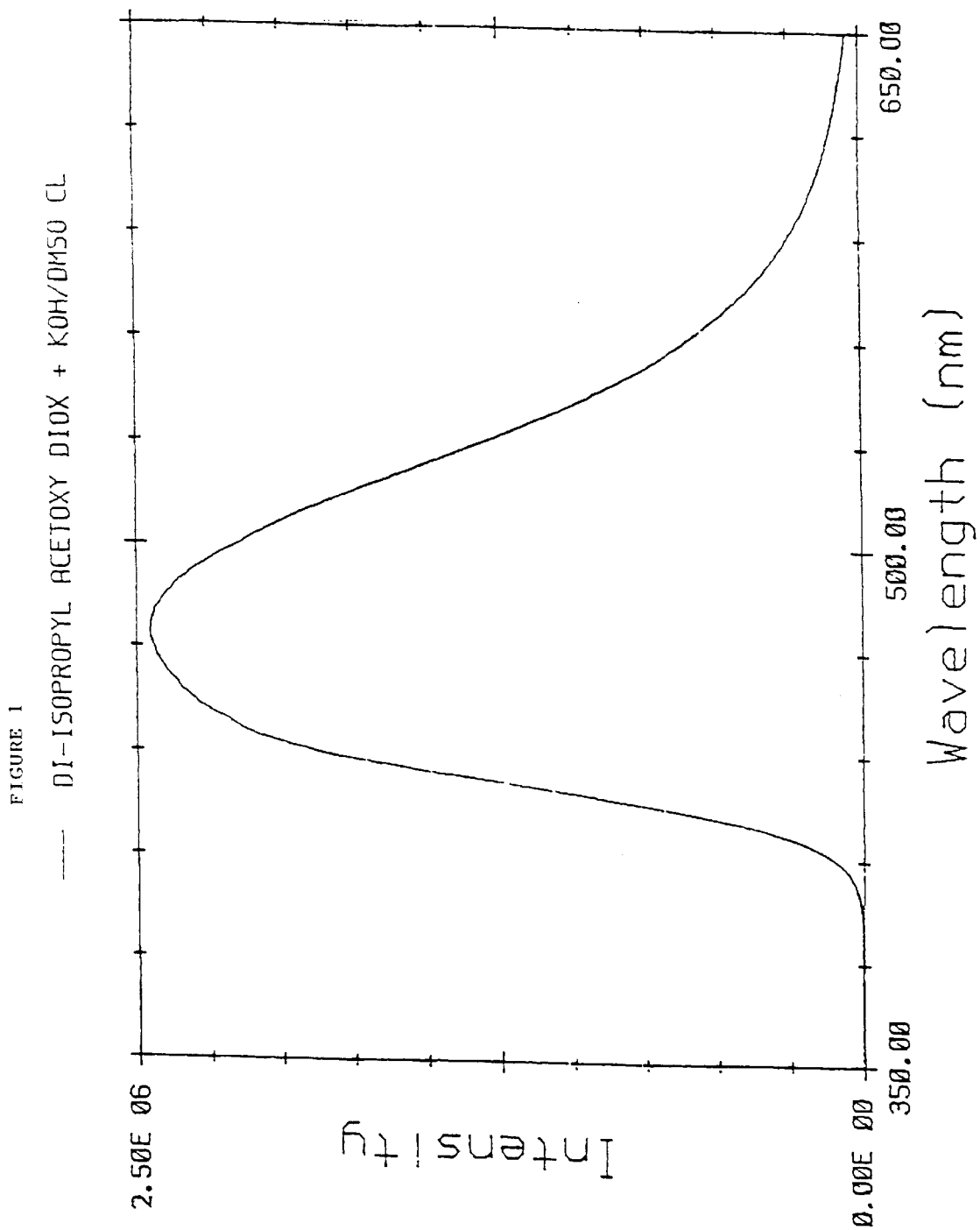
FIG. 1 is a spectrum of the chemiluminescence emitted from a solution of dioxetane 2c in dimethyl sulfoxide (DMSO) when triggered by addition of a solution of potassium hydroxide in a mixture of methanol and dimethyl sulfoxide. The spectrum is corrected for the decay in chemiluminescence intensity occurring during the scan.

Chemiluminescence and fluorescence spectra were measured using a Fluorolog II fluorimeter (Spex Ind., Edison, N.J.) with 1 cm quartz cuvettes. All measurements were performed at ambient temperature. The spectrum was either scanned when the light intensity reached a constant level or correction was made for the decay of light intensity during the scan. FIG. 1 shows a typical chemiluminescence spectrum from the decomposition of dioxetane 2c in DMSO triggered by addition of a small volume of a solution of KOH in 1:1 methanol/DMSO. The emission arises from the excited state of the anion of methyl 3-hydroxybenzoate. Triggered decomposition of each dioxetane of the present invention in DMSO generates this excited state.

Example 23

Chemical Triggering of the Chemiluminescent Decomposition of Dioxetanes 2c,g,i Stock solutions of dioxetanes 2c, 2e, 2g and for comparison, 4-(3-t-butyldimethylsilyloxyphenyl)-4-methoxyspiro[1,2-dioxetane-3,2'-tricyclo[3.3.1.1$^{3,7}$]decane] (2j), (preparation described in U.S. Pat. No. 4,962,192) were made to a concentration of 10$^6$ M in DMSO. Serial dilutions in DMSO were made as required. Ten μL aliquots were triggered in 7×50 mm polypropylene tubes in a Turner Designs TD-20e luminometer by injection of 50 μL of a solution of tetra-n-butylammonium fluoride (TBAF) in DMSO (1M–10$^{-4}$ M) in the appropriate solvent, typically DMSO. Light intensity was attenuated when needed by a neutral density filter. All experiments were conducted at ambient temperature. Peak light intensity and decay rate diminished as the fluoride concentration was decreased. At the lowest concentration of fluoride, decay kinetics were not cleanly first order.

Other triggering reagents found to produce chemiluminescence from dioxetanes 2a–e and 2g–i in DMSO or DMF include hydrazine, potassium and tetraalkylammonium hydroxides, alkali metal and tetraalkylammonium alkoxides and sodium azide. Small amounts (<5%) of a protic co-solvent such as methanol, ethanol or water could be used to dissolve the triggering agent in DMSO.

The duration and intensity of chemiluminescence may be altered by the choice of solvent, triggering agent and ratio of dioxetane/triggering agent. Suitable solvents for practicing the present invention include any aprotic solvent in which the reactants are soluble, especially polar solvents such as DMSO, dimethylformamide, acetonitrile, p-dioxane and the like. The reaction can also be conducted in, for example, a hydrocarbon solvent where only one of the reactants is dissolved and the other is supplied in the medium undissolved. In this case, light is emitted from the surface of the undissolved reactant.

Example 24

Rates of Triggered Decomposition of Dioxetanes 2c,h,i

Figure 2:
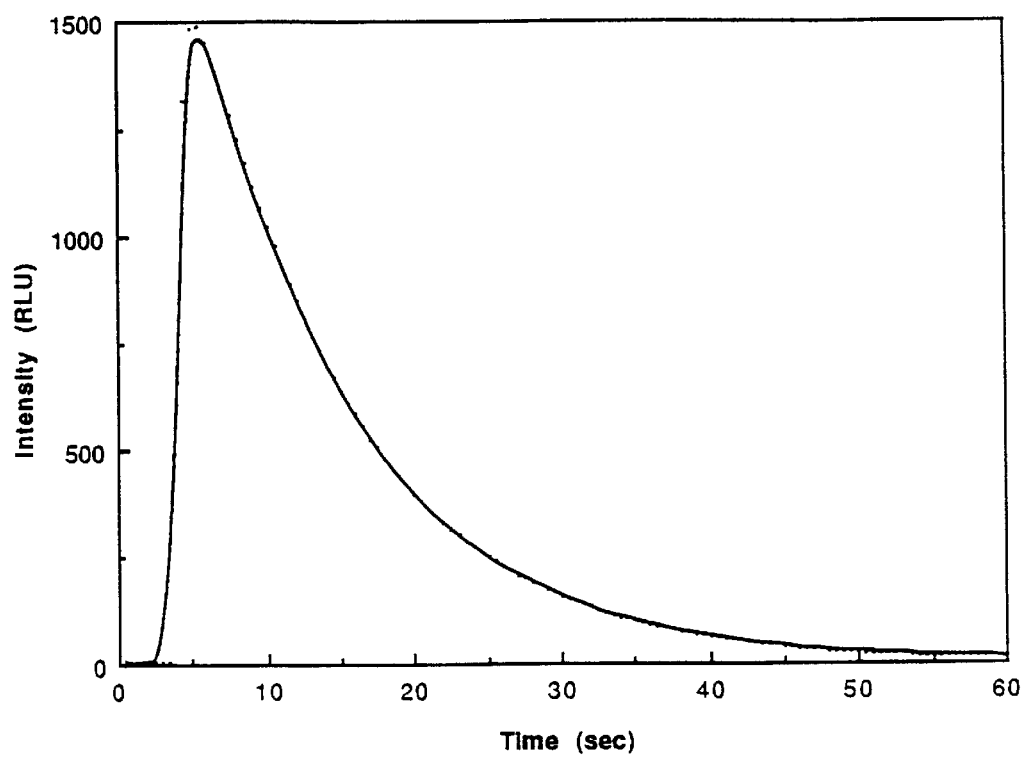
FIG. 2 is a graph of chemiluminescence intensity as a function of time produced by triggering a 10 $\mu$L aliquot of a $10^{-6}$ M solution of dioxetane 2 g with 50 $\mu$L of 1 M tetra-n-butylammonium fluoride in DMSO.

FIG. 2 shows a typical chemiluminescence intensity profile upon triggering a 10 μL aliquot of a $10^{-6}$ M solution of dioxetane 2h with 50 μL of 1 M TBAF in DMSO. Triggering of serial ten-fold dilutions of the dioxetane solution showed that a $10^{-9}$ M solution provided a signal 1.5 times that of background. All chemiluminescence decay curves showed pseudo-first order kinetics. The half lives for decay were essentially independent of dioxetane concentration.

TABLE 3

Rates and Chemiluminescence Intensity from Fluoride-triggered Decomposition of Dioxetane 2h as a Function of Concentration.

| [Dioxetane 2h] | [F⁻] | t½ (sec) | Total intensity |
|---|---|---|---|
| $10^{-6}$M | 1M | 7.2 | $1.9 \times 10^4$ TLU |
| $10^{-7}$M | 1M | 6.2 | $2.0 \times 10^3$ TLU |
| $10^{-8}$M | 1M | 6.2 | $2.1 \times 10^2$ TLU |
| $10^{-9}$M | 1M | 6.7 | $1.5 \times 10^1$ TLU |

The rates of fluoride-triggered decomposition of dioxetanes 2c, h, i and j were compared in DMSO under identical conditions, i.e. 10 μL aliquot of a $10^{-6}$ M solution of dioxetane with 50 μL of 1 M TBAF in DMSO. All four dioxetanes were found to undergo reaction at essentially the same rate under these conditions.

TABLE 4

Comparison of Thermal and Fluoride-triggered Decomposition Rates.

| Dioxetane | t½ trig. | t½ thermal | Rate acceleration |
|---|---|---|---|
| 2c | 7 sec | 1.2 yr | $5.5 \times 10^6$ |
| 2h | 7 sec | 1.7 yr | $7.0 \times 10^6$ |
| 2i | 6 sec | 1.1 yr | $5.7 \times 10^6$ |
| 2j | 7 sec | 3.8 yr | $1.4 \times 10^7$ |

Example 25

Measurement of Relative Chemiluminescence Quantum Yields

The total chemiluminescence intensity generated by fluoride-triggering of dioxetanes 2c, g, h and i were compared in DMSO under identical conditions, i.e. 10 μL aliquot of a $10^{-6}$ M solution of dioxetane with 50 μL of 1 M TBAF in DMSO. Precise values were difficult to reproduce; however, all four dioxetanes were found to generate the same chemiluminescence output within a factor of two under these conditions. Based on the reported chemiluminescence efficiency of 25% for dioxetane 2h (A. P. Schaap, T.-S. Chen, R. S. Handley, R. DeSilva and B. P. Giri, *Tetrahedron Lett.*, 1155 (1987)) the dioxetanes of the present invention are found to produce chemiluminescence with high efficiency upon triggering in DMSO.

Example 26

Comparison of Chemiluminescence Intensities-Kinetic Profile of Solutions Containing Dioxetane 2f or 2k

In order to demonstrate the unexpected advantage of the phosphate dioxetane 2f of the present invention, a comparison was made of the time course of chemiluminescence from this dioxetane induced by alkaline phosphatase (AP) in alkaline buffer solutions to the commercially available dioxetane 4-methoxy-4-(3-phosphoryloxyphenyl)spiro [1,2-dioxetane-3,2'-tricyclo[3.3.1.1$^{3,7}$]decane], disodium salt, (LUMIGEN PPD, Lumigen, Inc., Southfield, Mich.), dioxetane 2k. FIG. 3 illustrates the time profile and relative chemiluminescence intensities at 37° C. from two compositions, one containing 0.33 mM dioxetane 2d of the present invention and the other containing 0.33 mM dioxetane 2k in the same buffer. Light emission was initiated by addition of 1.12×10–17 moles of AP to 100 μL of the dioxetane solution. The reagent containing dioxetane 2f of the present invention reaches a significantly higher maximum intensity.

Example 27

Comparison of Chemiluminescence Intensities-Kinetic Profile of Solutions Containing Dioxetane 2f or 2k

FIG. 4 illustrates the time profile and relative chemiluminescence intensities at 37° C. from two compositions, one containing 0.33 mM dioxetane 2f of the present invention and 1.0 mg/mL of 1-(tri-n-octylphosphoniummethyl)-4-(tri-n-butylphosphoniummethyl)benzene dichloride (Enhancer A) and the other containing 0.33 mM dioxetane 2k and 1.0 mg/mL of the same enhancer. Light emission was initiated by addition of $1.12 \times 10^{-17}$ moles of AP to 100 μL of the dioxetane solution. The reagent containing dioxetane 2f of the present invention reaches achieves higher light intensities at all time points.

Example 28

Comparison of Chemiluminescence Intensities-Kinetic Profile of Solutions Containing Dioxetane 2f or 2k

FIG. 5 illustrates the time profile and relative chemiluminescence intensities at 37° C. from two compositions, one containing 0.33 mM dioxetane 2f of the present invention and 0.5 mg/mL of polyvinylbenzyltributylphosphonium chloride (Enhancer B) and the other containing 0.33 mM dioxetane 2k and 1.0 mg/mL of the same enhancer. Light emission was initiated by addition of $1.12 \times 10^{-17}$ moles of AP to 100 μL of the dioxetane solution. The reagent containing dioxetane 2f of the present invention reaches achieves higher light intensities at all time points.

Example 29

Comparison of Chemiluminescence Intensities-Kinetic Profile of Solutions Containing Dioxetane 2f or 2k

FIG. 6 illustrates the time profile and relative chemiluminescence intensities at 37° C. from two compositions, one containing 0.33 mM dioxetane 2f of the present invention and 0.5 mg/mL of polyvinylbenzyltributylphosphonium chloride co-polyvinylbenzyltrioctylphosphonium chloride (containing a 3:1 ratio of tributyl:trioctyl groups) (Enhancer C) and the other containing 0.33 mM dioxetane 2k and 0.5 mg/mL of the same enhancer. Light emission was initiated by addition of $1.12 \times 10^{-17}$ moles of AP to 100 μL of the dioxetane solution. The reagent containing dioxetane 2f of the present invention reaches achieves higher light intensities at all time points.

Example 30

Linearity and Sensitivity of Detection of Alkaline Phosphatase with Dioxetane 2f The linearity of detection of AP using a reagent composition of the present invention containing dioxetane 2f was determined. To each of 48 wells in a 96-well microplate was added 100 μL of a 0.33 mM solution of 2f in 0.2 M 2-methyl-2-amino-1-propanol buffer, pH 9.6 containing 0.88 mM $Mg^{+2}$ and 1.0 mg/mL of Enhancer A. The plate was incubated at 37° C. and chemiluminescence emission initiated by addition of 3 μL of solutions of AP containing between $3.36 \times 10^{-16}$ mol and $3.36 \times 10^{-22}$ mol of enzyme. Light intensities were measured at 10 min. FIG. 7 shows the linear detection of alkaline phosphatase. The term S-B refers to the chemiluminescence signal (S) in RLU in the presence of alkaline phosphatase (AP) corrected for background chemiluminescence (B) in the absence of AP. The calculated detection limit (twice the standard deviation of the background) was determined to be $2.0 \times 10^{-22}$ mol, or 120 molecules of AP under these conditions.

Example 31

Comparison of Chemiluminescence Quantum Yields

The relative chemiluminescence quantum yields of dioxetanes 2f and 2k were determined in solutions containing 1 mg/mL of Enhancer C in 0.2 M 2-amino-2-methyl-1-propanol buffer, pH 9.6 containing 0.88 mM $Mg^{+2}$ and selected enhancers as described in Table 4. A 100 μL aliquot of each reagent was completely dephosphorylated by addition of $3.36 \times 10^{-13}$ mol of alkaline phosphatase. The total amount of light emitted in Relative Light Units (RLU) was integrated until light emission ceased. A similar comparison was also made with 500 μL portions of formulations without any enhancer using either 0.2 M or 0.75 M 2-amino-2-methyl-1-propanol buffer, pH 9.6 containing 0.88 mM $Mg^{+2}$. Dioxetane 2f produces more light than dioxetane 2k in buffer alone and in the presence of Enhancers A and C.

TABLE 5

Total Light Intensity from Phosphate Dioxetanes

| Enhancer | Dioxetane 2f | Dioxetane 2k |
|---|---|---|
| None (0.2M) | $2.82 \times 10^5$ | $1.55 \times 10^5$ |
| None (0.75M) | $5.55 \times 10^4$ | $4.41 \times 10^4$ |
| Enhancer A (1 mg/mL) | $1.19 \times 10^7$ | $9.0 \times 10^6$ |
| Enhancer B (0.5 mg/mL) | $1.65 \times 10^6$ | $2.09 \times 10^6$ |
| Enhancer C (0.5 mg/mL) | $4.15 \times 10^7$ | $3.65 \times 10^7$ |

Example 32

Stability of Dioxetane 2f in Aqueous Solutions

The thermal and hydrolytic stability of a 0.33 mM solution of dioxetane 2f containing 1 mg/mL of Enhancer A in 0.2 M 2-amino-2-methyl-1-propanol buffer, pH 9.6 and 0.88 mM $Mg^{+2}$ was determined at 37° C. Solutions of the dioxetane were maintained at room temperature and 37° C. for 5 days. To each of 12 wells in a 96-well microplate was added 100 μL of each solution. The plate was incubated at 37° C. and chemiluminescence emission initiated by addition of 10 μL of solutions containing $1.1 \times 10^{-15}$ mol of AP. Light intensities were integrated for 2.5 hours. Stability of the dioxetane was assessed by comparing the average light yield of the sample incubated at 37° C. to the solution held at room temperature. A decrease in the amount of light emitted indicates decomposition of the dioxetane during the incubation period. The solution maintained at 37° C. was identical to the room temperature solution indicating the dioxetane to be stable under these conditions.

Example 33

Chemiluminescent Detection of Alkaline Phosphatase on Membrane

The utility of a composition of the present invention for the chemiluminescent detection of enzymes on the surface of blotting membranes is demonstrated in the following example. Solutions of alkaline phosphatase in water containing from 1.1 fmol to 1.1 amol were applied to identical nylon membranes (Micron Separations Inc., Westboro, Mass.). The membranes were air dried for 5 min and soaked briefly with a reagent containing 1 mg/mL of Enhancer A in 0.2 M 2-amino-2-methyl-1-propanol buffer, pH 9.6 containing 0.88 mm MgCl and either 0.33 mM dioxetane 2f or 0.33 mM dioxetane 2k. The membranes were placed between transparency sheets and exposed to X-ray film (Kodak X-OMAT AR, Rochester, N.Y.). FIGS. 8A and 8B show that the light produced using the two dioxetanes led to equivalent images and detection sensitivity. These results illustrate the performance of dioxetane 2f which is to be expected in Western blotting, Southern blotting, DNA fingerprinting and other blotting applications.

We claim:

1. A stable 1,2-dioxetane compound of the formula:

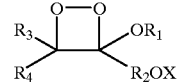

wherein $R_1$ is selected from alkyl and cycloalkyl groups containing 1 to 12 carbon atoms which can additionally contain heteroatoms, wherein $R_2$ is a meta-phenyl group substituted by the OX group in the position meta to the dioxetane ring, wherein $R_3$ and $R_4$ are selected independently from branched alkyl and cycloalkyl groups containing 3 to 8 carbons atoms which can additionally contain heteroatoms and which provide thermal stability, and wherein X is a chemically labile group selected from the group consisting of trialkylsilyl and $PO_3^{2-}$ salt, which can be removed by a reagent selected from the group consisting of enzymes, electron donors, organic and inorganic bases, nucleophilic reagents and reducing agents to form an unstable oxide intermediate 1,2-dioxetane compound which decomposes to form light and two carbonyl compounds of the formula:

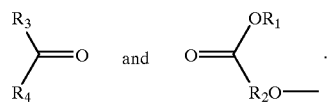

2. The dioxetane of claim 1 wherein $R_3$ and $R_4$ are independently selected from branched chain alkyl and cycloalkyl groups containing 3 to 8 carbon atoms.

3. The dioxetane of claim 2 wherein $R_3$ and $R_4$ are each isopropyl groups.

4. The dioxetane of claim 2 wherein $R_3$ and $R_4$ are each cyclohexyl groups.

5. The dioxetane of claim 2 wherein $R_3$ and $R_4$ are each cyclopropyl groups.

6. The dioxetane of claim 1 having the formula:

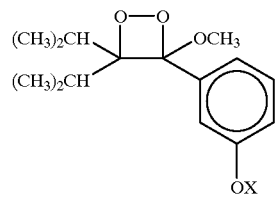

7. The dioxetane of claim 1 having the formula:

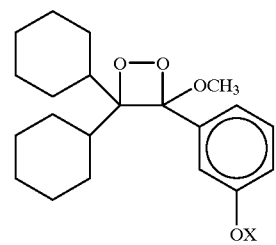

8. The dioxetane of claim 1 having the formula:

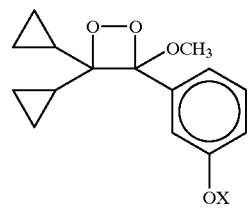

9. A dioxetane compound having the formula:

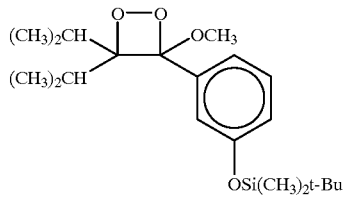

10. A dioxetane compound having the formula:

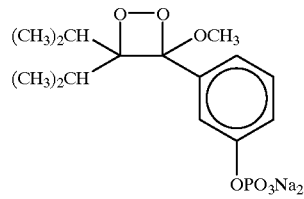

11. A dioxetane compound having the formula:

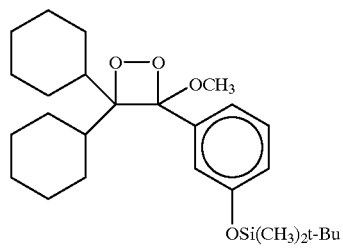

12. A dioxetane compound having the formula:

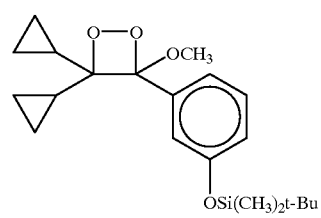

13. A 1,2-dioxetane compound of the formula:

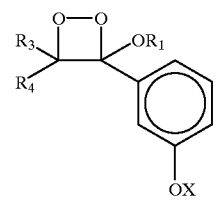

wherein $R_1$ represents a substituted or unsubstituted alkyl or cycloalkyl group; $R_3$ and $R_4$ each represent, individually, a substituted or unsubstituted branched alkyl or cycloalkyl group; and X represents trialkylsilyl or a $PO_3^{2-}$ salt group.

14. The 1,2-dioxetane compound of claim 13, wherein $R_1$ contains from 1 to 12 carbon atoms.

15. The 1,2-dioxetane compound of claim 14, wherein $R_1$ is methyl.

16. The 1,2-dioxetane compound of claim 13, wherein $R_1$ contains at least one heteroatom.

17. The 1,2-dioxetane compound of claim 13, wherein each of $R_3$ and $R_4$ has from 3 to 8 carbon atoms.

18. The 1,2-dioxetane compound of claim 13, wherein at least one of $R_3$ and $R_4$ contains a heteroatom.

19. The 1,2-dioxetane compound of claim 17, wherein $R_3$ and $R_4$ are each cyclohexyl groups.

20. The 1,2-dioxetane compound of claim 17, wherein $R_3$ and $R_4$ are each isopropyl groups.

21. The 1,2-dioxetane compound of claim 17, wherein $R_3$ and $R_4$ are each cyclopropyl groups.

22. The 1,2-dioxetane compound of claim 13, wherein X is a $PO_3^{2-}$ salt group.

23. The 1,2-dioxetane compound of claim 22, wherein the $PO_3^{2-}$ salt group is —$PO_3Na_2$.

24. The 1,2-dioxetane compound of claim 13, wherein X is trialkylsilyl.

25. The 1,2-dioxetane compound of claim 24, wherein the trialkylsilyl is —$Si(CH_3)_2$t-Bu.

26. The 1,2-dioxetane compound of claim 13, having the formula:

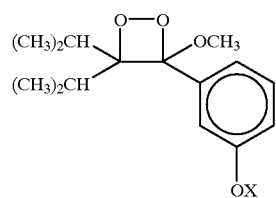
27. The 1,2-dioxetane compound of claim 13, having the formula:
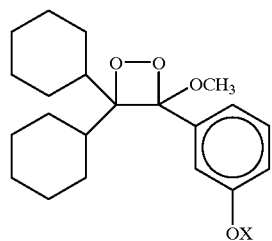
28. The 1,2-dioxetane compound of claim 13, having the formula:
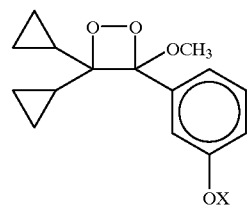
29. The 1,2-dioxetane compound of claim 13, which is:
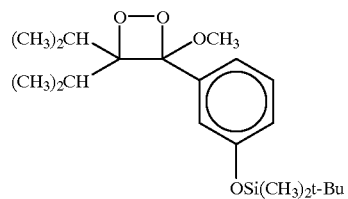
30. The 1,2-dioxetane compound of claim 13, which is:
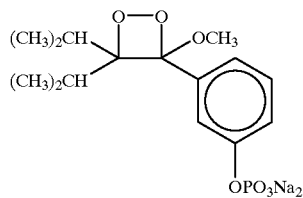
31. The 1,2-dioxetane compound of claim 13, which is:
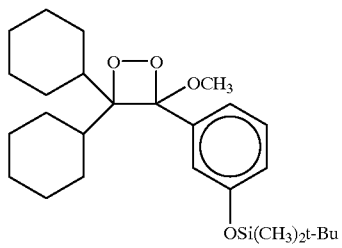
32. The 1,2-dioxetane compound of claim 13, which is:
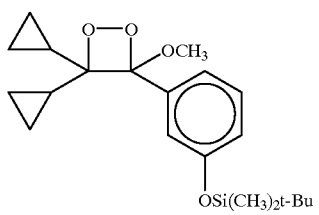
* * * * *